(12) United States Patent
Mechetner et al.

(10) Patent No.: US 6,630,327 B1
(45) Date of Patent: Oct. 7, 2003

(54) METHODS AND REAGENTS FOR PREPARING AND USING IMMUNOLOGICAL AGENTS SPECIFIC FOR P-GLYCOPROTEIN

(75) Inventors: Eugene Mechetner, Irvine, CA (US); Igor B. Roninson, Wilmette, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/397,233

(22) Filed: Sep. 16, 1999

Related U.S. Application Data

(62) Division of application No. 08/752,447, filed on Nov. 15, 1996, now Pat. No. 5,994,088.

(51) Int. Cl.[7] .................. C12P 21/04; C12N 15/09; C12N 15/00; C12N 15/06; C07K 16/28
(52) U.S. Cl. .................. 435/69.6; 435/69.1; 435/69.3; 435/70.1; 435/70.2; 435/440; 435/449; 435/452; 435/451; 435/325; 530/387.1; 530/387.7; 530/387.9; 530/388.1; 530/388.2
(58) Field of Search .................. 435/7.21, 330, 435/344, 344.1, 325, 346, 452, 449, 451, 69.1, 69.3, 69.6, 70.1, 70.2, 440; 530/387.1, 387.7, 387.9, 388.1, 388.2, 388.8, 389.1, 389.7, 403

(56) References Cited

U.S. PATENT DOCUMENTS

| | | | |
|---|---|---|---|
| 4,837,306 A | | 6/1989 | Ling et al. |
| 4,918,163 A | | 4/1990 | Young et al. |
| 4,925,787 A | | 5/1990 | Tanihara et al. |
| 5,057,598 A | | 10/1991 | Pollack et al. |
| 5,061,620 A | | 10/1991 | Tsukamoto et al. |
| 5,091,513 A | | 2/1992 | Huston et al. |
| 5,130,127 A | | 7/1992 | Herlyn |
| 5,132,405 A | | 7/1992 | Huston et al. |
| 5,134,075 A | | 7/1992 | Hellstrom et al. |
| 5,204,095 A | | 4/1993 | Goodall et al. |
| 5,206,352 A | | 4/1993 | Roninson et al. |
| 5,215,913 A | | 6/1993 | Posner et al. |
| 5,434,075 A | * | 7/1995 | Mechetner et al. ......... 435/240 |
| 5,464,753 A | | 11/1995 | Chaudhary et al. |
| 6,063,621 A | * | 5/2000 | Deeley et al. ............. 435/330 |

FOREIGN PATENT DOCUMENTS

| | | | |
|---|---|---|---|
| WO | WO 93 19094 A1 | | 9/1993 |
| WO | 21325 | * | 5/1998 |

OTHER PUBLICATIONS

Lodish, H., et al., 2000, Molecular Cell Biology, W.H. Freeman & Co., 4th Edition, p. 54.*
Mechetner et al PNAS vol. 89 p. 5824 (7/92).*
Meyers et al Proc. Am. Assoc. Cancer Res. vol. 29, p. 295, abstract No. 1172 (3/98).*
Rittmann–Grauer et al Proc. Am. Assoc. Cancer Res. vol. 28 p. 394, abstract No. 1564 (3/87).*
Burgess et al, J. Cell Biology vol. 111 p. 2129 (1990).*
Lazar et al, Mol. and Cell. Biol. vol. 8 p. 1247 (1988).*
Akiyama et al., Molec. Pharm. 33:144(1988).
Arcesi et al., Cancer Res. 53:310–317(1993).
Ball et al., 1990 Blood 76(10, Suppl 1):252a.
Barth et al., 1991, J. Exp. Med. 173:647–658.
Beck et al., J. Natl. Cancer Inst. 83:1364–1366.
Chaudhary et al., Cell 66:85 (1991).
Chaudhary et al., Blood 80:2735 (1992).
Chen et al., Cell 47:381 (1986).
Choi et al., Cell 53:519–529 (1988).
Choi et al., Proc. Natl. Acad. Sci. USA 88:7386–7390 (1991).
Co & Queen, 1991 Nature 351:501–502.
Coon et al., Human Immunol. 32:134 (1991).
Cordon–Cardo et al. J. Histochem. Cytochem 38:1277 (1990).
Cornwell et al., J. Bio. Chem. 261:7921 (1986).
Dillman et al., Annals. Of Internal Med. 111(7):592 (1989).
Drach et al., Blood 80:2729 (1992).
Efferth et al., 1989, Anti. Cancer Research 9:1633–1638.
Endicott & Ling, Annu. Rev. Biochem, 58:137 (1989).
Ford et al., Pharm. Rev. 42:155 (1990).
Georges et al. PNAS (USA) 87:152–156 (1990).
Gillies et al., Human Antibod. Hybridons 1(1):47 (1990).
Gillis, 1989, Fundamental Immunology, 2d ed., Raven Press, N.Y., pp. 621–638.
Gottesman & Pastan., Annu. Rev. Biochem, 62:385 (1993).
Gros et al., Proc. Natl. Acad. Sci. USA 83:337 (1986).
Gupta et al., J. Clin. Immunol. 13:289 (1990).
Hamada et al., PNAS 83:7785–7789 (1986).
Hamada et al., 1990, Cancer Res. 50:3167.
Heike et al., Jpn. J. Cancer Res. 81:1155–61 (1990).
Higgins, Annu. Rev. Cell Biol. 8:67 (1992).
Hoogenboom et al., Nucleic Acids Research 19(15):4133–4137.
Takeda et al., Proc. Natl. Acad. Sci. USA 84:3580 (1988).
Klimecki et al., Blood 83:2451 (1994).
Kobayashi et al., Biochem. Pharmacol. 48:1641 (1994).
Kronke et al., Proc. Natl. Sci. USA 81:5214–5218 (1984).
Kramer et al., Nucleic Acids Res. 12:9441–9456 (1984).
Kuwazuru et al., Cancer 66(5):868 (1990).

(List continued on next page.)

*Primary Examiner*—Sheela Huff
(74) *Attorney, Agent, or Firm*—McDonnell Boehnen Hulbert & Berghoff

(57) ABSTRACT

This invention relates to immunological reagents and methods specific for a mammalian, transmembrane protein termed Pgp, having a non-specific efflux pump activity established in the art as being a component of clinically-important multidrug resistance in cancer patients undergoing chemotherapy. The invention provides methods for developing and using immunological reagents specific for certain mutant forms of Pgp and for wild-type Pgp in a conformation associated with substrate binding or in the presence of ATP depleting agents. The invention also provides improved methods for purifying hematopoietic stems cells expressing Pgp and diagnostic and therapeutic methods for cancer cells expressing Pgp.

3 Claims, 34 Drawing Sheets

OTHER PUBLICATIONS

Lazar et al., Molecular and Cellular Biology 8(3):1247–1252 (1988).
Lokhorst et al., Cancet Treatment Reviews 19:113–128 (1993).
Maino et al., Cytometry 20: 127–133 (1995).
McCafferty et al., Nature 348:552–554 (1990).
McDuffie, Am. J. Med. 78(1A): 1–5 (Jan. 21, 1985).
McGrath, Nature 340:400 (1989).
Mechetner et al., Proc. Natl. Acad. Sci, USA 89:5824–5828 (1992).
Meyers et al., Cancer Research 49:3209–3214 (1989).
Mulder et al., 1987, Exp. Hematol, 15:99–104.
Muller et al., J. Biol. Chem. 271:1877–1882 (1996).
Neyfakh et al., Exp. Cell. Res. 185:496–505 (1989).
Neyfakh et al., Exp. Cell. Res. 174:168–176 (1988).
Noonan et al., Proc. Natl. Acad. Sci. USA 87:7160–7164 (1990).
O'Brien et al., Proc. Amer. Assoc. Cancer Res. 30:Abs. 2114 (1989).
Pearson et al., J. Nat'l Cancer Inst. 88:1386 (1991).
Ploemacher et al., Exp. Hematol 17:263–266 (1989).
Rittman–Grauer, Proc. Amer. Assoc. Cancer Res. 31:Abs. 2663–(1990).
Salmon et al., Blood 78(1):44–50 (1991).
Schluesener et al., Immunopharmacology 23:37.
Schwartz and Datta, 1989, Fundamental Immunology, 2d ed., Raven Press, N.Y. p. 819–866.
Shen et al., Molecular and Cellular Biology 6(11): 4039–4045 (1986).
Spangrade et al., 1990, Proc. Natl. Acad. Sci. USA 87:7433–7437.
Spangrade, 1989, Eisevier Science Publishers Ltd., UK, p. 344.
Srour et al., Experimental Hematology 20:734 (1992). No. 117.
Srour et al., 1990, Exp. Hemotol. 18:549, Abstract #3.
Srour et al., 1991, Cytometry 12:179–183.
Tamai, J. Biochem, Molec. Biol. 265:16509 (1990).
Tao et al., Journal of Immunology 143(8):2595 (1989).
Thiebaut et al., Proc. Natl. Acad. Sci. USA 84:7735 (1987).
Thorpe, Monoclonal Antibodies 84:475–506 (1985).
Tiirikainen et al., Ann. Hematol. 65:124 (1992).
Trail et al., 1993 Sciences 261:212–215.
Tsuro et al., Jpn. J. Cancer Res. 80:627 (1989).
Van der Bliek et al., 1989, Advances in Cancer Research 52:165.
Van der Sluijs et al., 1990, Exp. Hematol 18:893–896.
Van Duk et al., Int. J. Cancer 44:738–743 (1989).
Visser et al., 1990, Exp. Hematol. 18:248–256.
Waldmann, Science 252:1657 (1991).
Weisberg et al., J. Exp Med. 183:2699–2704 (1996).
Winter et al., Annu. Rev. Immunology, 12:433–455 (1994).
Witkowski et al., J. Immunol. 153:658 (1994).

* cited by examiner

FIG. 1A

```
  1  CCTACTCTAT  TCAGATATTC  TCAGATATTC  AGATCATTTC
 51  TCATTCCCT   AGGAGTACTC  ACTTCAGGAT  GCAACCAGAT  GTTTCGCAGT
101  TGCAACGGAA  GCCAGAACAT  TCCTCCTGGA  AATTCAACCT  GTTTCGCAGT
151  TTCTCGAGGA  ATCAGCATTC  AGTCAATCCG  GGCCGGGAGC  AGTCATCTGT
201  GGTGAGGCTG  ATTGGCTGGG  CAGGAACAGC  GCCGGGGCGT  GGGCTGAGCA
251  CAGCGCTTCG  CTCTCTTTGC  CACAGGAAGC  CTGAGCTCAT  TCGAGTAGCG
301  GCTCTTCCAA  GCTCAAAGAA  GCAGAGGCCG  CTGTTCGTTT  CCTTTAGGTC
351  TTTCCACTAA  AGTCGGAGTA  TCTTCTTCCA  AGATTTCACG  TCTTGGTGGC
401  CGTTCCAAGG  AGCGCGAGGT  CGGGATGGAT  CTTGAAGGGG  ACCGCAATGG
451  AGGAGCAAAG  AAGAAGAACT  TTTTTAAACT  GAACAATAAA  AGTGAAAAAG
501  ATAAGAAGGA  AAAGAAACCA  ACTGTCAGTG  TATTTCAAT   GTTTCGCTAT
551  TCAAATTGGC  TTGACAAGTT  GTATATGGTG  GTGGGAACTT  TGGCTGCCAT
```

FIG. 1B

```
 601  CATCCATGGG  GCTGGACTTC  CTCTCATGAT  GCTGGTGTTT  GGAGAAATGA
 651  CAGATATCTT  TGCAAATGCA  GGAAATTTAG  AAAGATCTGAT GTCAAACATC
 701  ACTAATAGAA  GTGATATCAA  TGATACAGGG  TTCTTCATGA  ATCTGGAGGA
 751  AGACATGACC  AGGTATGCCT  ATTATTACAG  TGGAATTGGT  GCTGGGGTGC
 801  TGGTTGCTGC  TTACATTCAG  GTTTCATTTT  GGTGCCTGGC  AGCTGGAAGA
 851  CAAATACACA  AAATTAGAAA  ACAGTTTTTT  CATGCTATAA  TGCGACAGGA
 901  GATAGGCTGG  TTTGATGTGC  ACGATGTTGG  GGAGCTTAAC  ACCCGACTTA
 951  CAGATGATGT  CTCCAAGATT  AATGAAGGAA  TTGGTGACAA  AATTGGAATG
1001  TTCTTTCAGT  CAATGGCAAC  ATTTTTCACT  GGGTTTATAG  TAGGATTTAC
1051  ACGTGGTTGG  AAGCTAACCC  TTGTGATTTT  GGCCATCAGT  CCTGTTCTTG
1101  GACTGTCAGC  TGCTGTCTGG  GCAAAGATAC  TATCTTCATT  TACTGATAAA
1151  GAACTCTTAG  CGTATGCAAA  AGCTGGAGCA  GTAGCTGAAG  AGGTCTTGGC
```

FIG. 1C

| | | | | |
|---|---|---|---|---|
| 1201 | AGCAATTAGA | ACTGTGATTG | CATTTGGAGG | ACAAAAGAAA | GAACTTGAAA |
| 1251 | GGTACAACAA | AAATTTAGAA | GAAGCTAAAA | GAATTGGGAT | AAAGAAAGCT |
| 1351 | TTATGCTCTG | GCCTTCTGGT | ATGGGACCAC | CTTGGTCCTC | TCAGGGGAAT |
| 1401 | ATTCTATTGG | ACAAGTACTC | ACTGTATTCT | TTTCTGTATT | AATTGGGCT |
| 1451 | TTTAGTGTTG | GACAGGCATC | TCCAAGCATT | GAAGCATTG | CAAATGCAAG |
| 1501 | AGGAGCAGCT | TATGAAATCT | TCAAGATAAT | TGATAATAAG | CCAAGTATTG |
| 1551 | ACAGCTATTC | GAAGAGTGGG | CACAAACCAG | ATAATATTAA | GGGAAATTTG |
| 1601 | GAATTCAGAA | ATGTTCACTT | CAGTTACCCA | TCTCGAAAAG | AAGTTAAGAT |
| 1651 | CTTGAAGGGC | CTGAACCTGA | AGGTGCAGAG | TGGGCAGACG | GTGGCCCTGG |
| 1701 | TTGGAAACAG | TGGCTGTGGG | AAGAGCACAA | CAGTCCAGCT | GATGCAGAGG |
| 1751 | CTCTATGACC | CCACAGAGGG | GATGGTCAGT | GTTGATGGAC | AGGATATTAG |
| 1801 | GACCATAAAT | GTAAGGTTTC | TACGGGAAAT | CATTGGTGTG | GTGAGTCAGG |

FIG. 1D

```
1851  AACCTGTATT  GTTTGCCACC  ACGATAGCTG  AAAACATTCG  CTATGGCCGT
1901  GAAAATGTCA  CCATGGATGA  GATTGAGAAA  GCTGTCAAGG  AAGCCAATGC
1951  CTATGACTTT  ATCATGAAAC  TGCCTCATAA  ATTTGACACC  CTGGTTGGAG
2001  CGTGCCCTGG  TTCGCAACCC  CAAGATCCTC  CTGCTGGATG  AGGCCACGTC
2051  AGCCTTGGAC  ACAGAAAGCG  AAGCAGTGGT  TCAGGTGGCT  CTGGATAAGG
2101  CCAGAAAAGG  TCGGACCACC  ATTGTGATAG  CTCATCGTTT  GTCTACAGTT
2151  CGTAATGCTG  ACGTCATCGC  TGGTTTCGAT  GATGGAGTCA  TTGTGGAGAA
2201  AGGAAATCAT  GATGAACTCA  TGAAAGAGAA  AGGCATTTAC  TTCAAACTTG
2251  TCACAATGCA  GACAGCAGGA  AATGAAGTTG  AATTAGAAAA  TGCAGCTGAT
2301  GAATCCAAAA  GTGAAATTGA  TGCCTTGGAA  ATGTCTTCAA  ATGATTCAAG
2351  ATCCAGTCTA  ATAAGAAAAA  GATCAACTCG  TAGGAGTGTC  CGTGGATCAC
2401  AAGCCCAAGA  CAGAAAGCTT  AGTACCAAAG  AGGCTCTGGA  TGAAAGTATA
```

FIG. 1E

```
2501  CCTCCAGTTT  CCTTTTGGAG  GATTATGAAG  CTAAATTTAA  CTGAATGGCC
2551  TTATTTTGTT  GTTGGTGTAT  TTTGTGCCAT  TATAAATGGA  GGCCTGCAAC
2601  CAGCATTTGC  AATAATATTT  TCAAAGATTA  TAGGGGTTTT  TACAAGAATT
2651  GATGATCCTG  AAACAAAACG  ACAGAATAGT  AACTTGTTTT  CACTATTGTT
2701  TCTAGCCCTT  GGAATTATTT  CTTTTRTTAC  ATTTTTCCTT  CAGGGTTTCA
2751  CATTTGGCAA  AGCTCCAGAG  ATCCCTCACCA  AGCGGCTCCG  ATACATGTT
2801  TTCCGATCCA  TGCTCAGACA  GGATGTGAGT  TGTTTGATG   ACCCTAAAAA
2851  CACCACTGGA  GCATTGACTA  CCAGGCTCGC  CAATGATGCT  GCTCAAGTTA
2901  AAGGGGCTAT  AGGTTCCAGG  CTTGCTGTAA  TTACCCAGAA  TATAGCAAAT
2951  CTTGGGACAG  GAATAATTAT  ATCCTTCATC  TATGGTTGGC  AACTAACACT
3001  GTTACTCTTA  GCAATTGTAC  CCATCATTGC  AATAGCAGGA  GTTGTTGAAA
3051  TGAAAATGTT  GTCTGGACAA  GCACTGAAAG  ATAAGAAAGA  ACTAGAAAAA
```

FIG. 1F

```
3101  GCTGGGAAGA  TCGCTACTGA  AGCAATAGAA  AACTTCCGAA  CCGTTGTTTC
3151  TTTGACTCAG  GAGCAGAAGT  TTGAACATAT  GTATGCTCAG  AGTTTGCAGG
3201  TACCATACAG  AAACTCTTTG  AGGAAAGCAC  ACATCTTTGG  AATTACATTT
3251  TCCTTCACCC  AGGCAATGAT  GTATTTTTCC  TATGCTGGAT  GTTTCCGGTT
3301  TGGAGCCTAC  TTGGTGGCAC  ATAAACTCAT  GAGCTTTGAG  GATGTTCTGT
3351  TCATTTGCTC  CTGACTATGC  CAAAGCCAAA  ATATCAGCAG  CCCACATCAT
3451  CATGATCATT  GAAAAAACCC  CTTTGATTGA  CAGCTACAGC  ACGGAAGGCC
3501  TAATGCCGAA  CACATTGGAA  GGAAATGTCA  CATTGGTGA  AGTTGTATTC
3551  AACTATCCCA  CCCGACCGGA  CATCCCAGTG  CTTCAGGGAC  TGAGCCTGA
3601  GGTGAAGAAG  GGCCAGACGC  TGGCTCTGGT  GGGCAGCAGT  GGCTGTGGGA
3651  AGAGCACAGT  GGTCCAGCTC  CTGGAGCGGT  TCTACGACCC  CTTGGCAGGG
3701  AAAGTGCTGC  TTGATGGCAA  AGAAATAAAG  CGACTGAATG  TTCAGTGGCT
```

FIG. 1G

```
3751  CCGAGCACAC  CTGGGCATCG  TGTCCCAGGA  GCCCATCCTG  TTTGACTGCA
3801  GCATTGCTGA  GAACATTGCC  TATGGAGACA  ACAGCCGGGT  GGTGTCACAG
3851  GAAGAGATCG  TGAGGGCAGC  AAAGGAGGCC  AACATACATG  CCTTCATCGA
3901  GTCACTGCCT  AATAAATATA  GCACTAAAGT  AGGAGACAAA  GGAACTCAGC
3951  TCTCTGGTGG  CCAGAAACAA  CGCATTGCCA  TAGCTCGTGC  CCTTGTTAGA
4001  CAGCCCTCATA  TTTTGCTTTT  GGATGAAGCC  ACGTCAGCTC  TGGATACAGA
4051  AAGTGAAAAG  GTTGTCCAAG  AAGCCCTGGA  CAAAGCCAGA  GAAGGCCGCA
4101  CCTGCATTGT  GATTGCTCAC  CGCCTGTCCA  CCATCCAGAA  TGCAGACTTA
4151  ATAGTGGTGT  TTCAGAATGG  CAGAGTCAAG  GAGCATGGCA  CGCATCAGCA
4201  GCTGCTGGCA  CAGAAAGGCA  TCTATTTTTC  AATGGTCAGT  GTCCAGGCTG
4251  GAACAAAGCG  CCAGTGAACT  CTGACTGTAT  GAGATGTTAA  ATACTTTTA
4301  ATATTTGTTT  AGATATGACA  TTTATTCAAA  GTTAAAAGCA  AACACTTACA
```

FIG. 1H

```
4351  GAATTATGAA  GAGGTATCTG  TTTAACATTT  CCTCAGTCAA  GTTCAGAGTC
4401  TTCAGAGACT  TCGTAATTAA  AGGAACAGAG  TGAGAGACAT  CATCAAGTGG
4451  AGAGAAATCA  TAGTTTAAAC  TGCATTATAA  ATTTTATAAC  AGAATTAAAG
4501  TAGATTTAA   AAGATAAAAT  GTGTAATTTT  GTTTATATTT  TCCCATTTCG
4551  ACTGTAACTG  ACTGCCTTGC  TAAAAGATTA  TAGAAGTAGC  AAAAAGTATT
4601  GAAATGTTTG  CATAAAGTGT  CTATAATAAA  ACTAAACTTT  CATGTGAAAA
4651  AAAAAAAAAA  AAAAAAAA
```

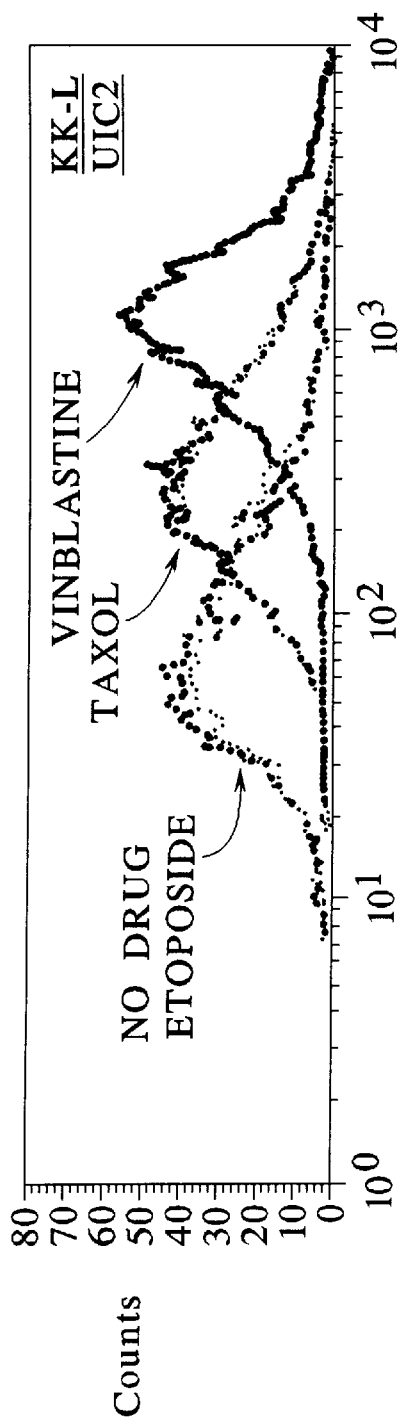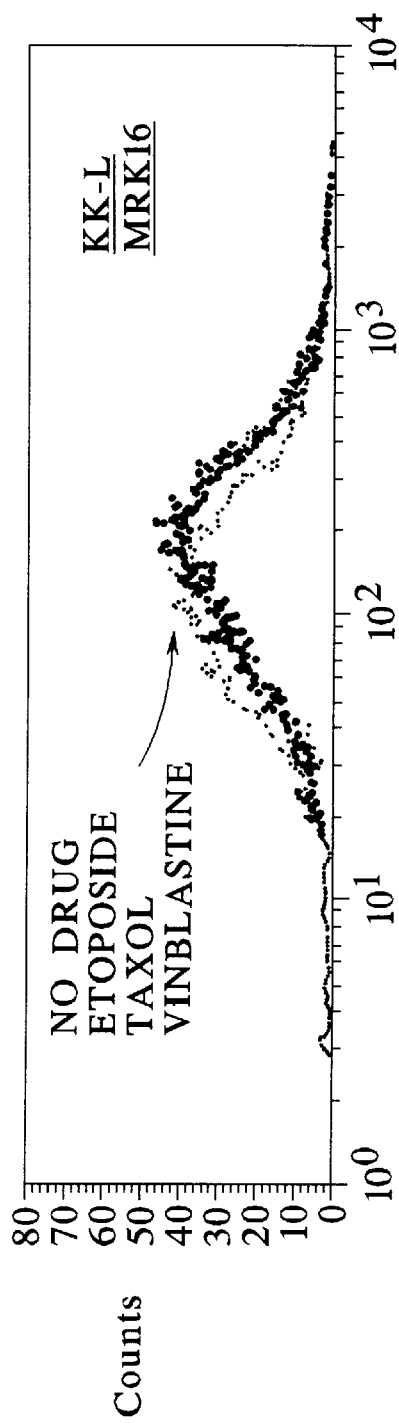

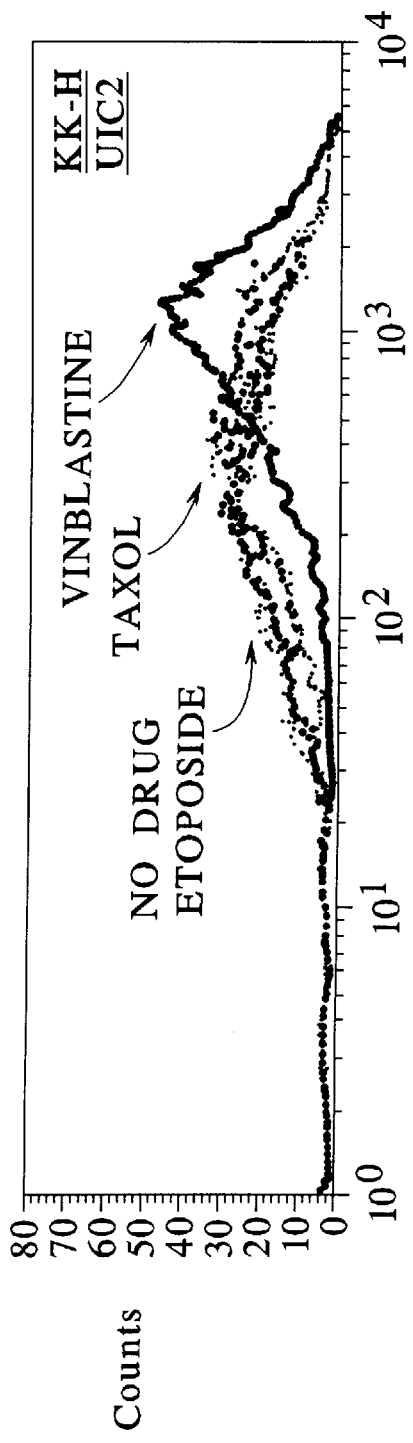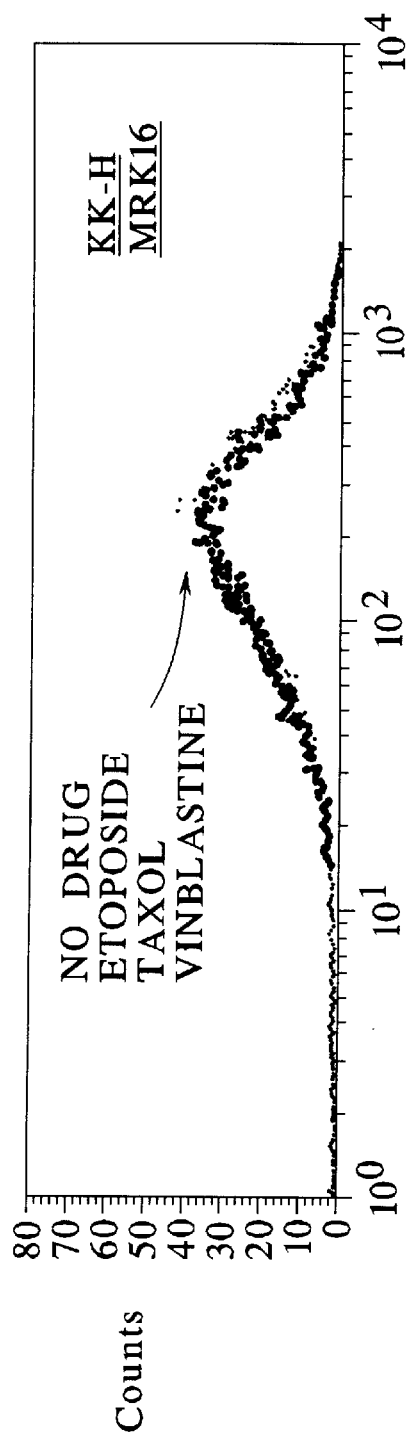
FIG. 7A
FIG. 7B

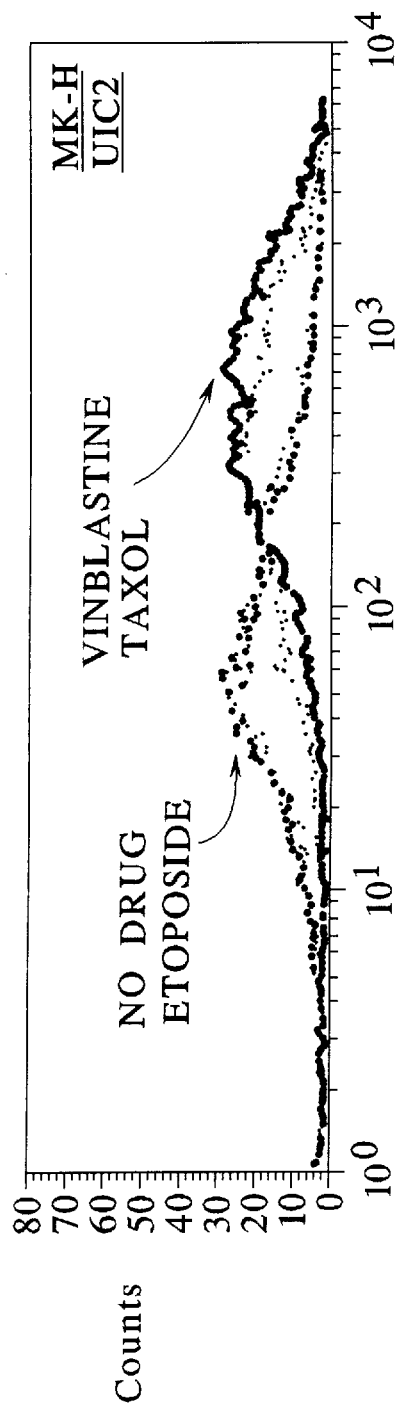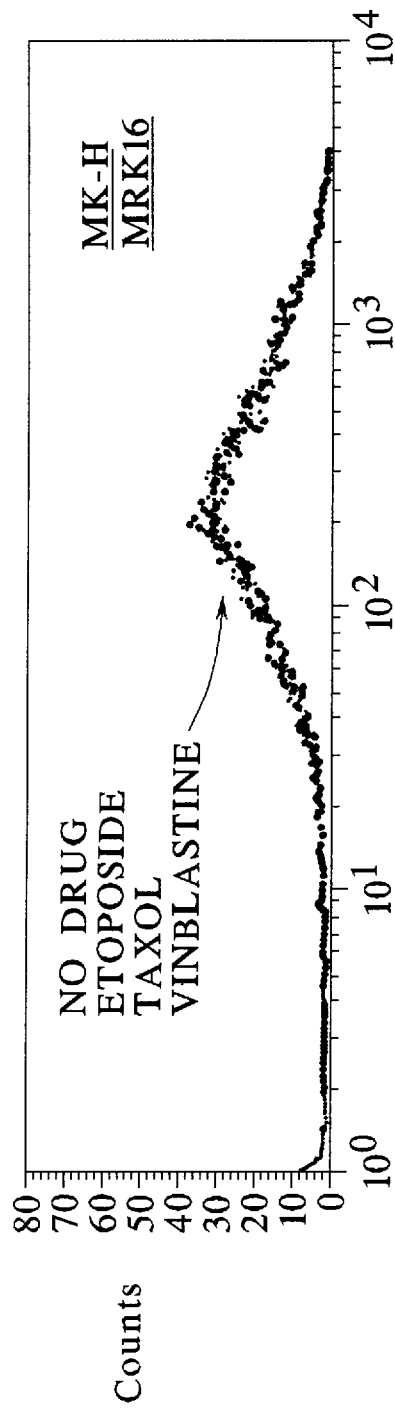

FIG. 8 CONT.
C
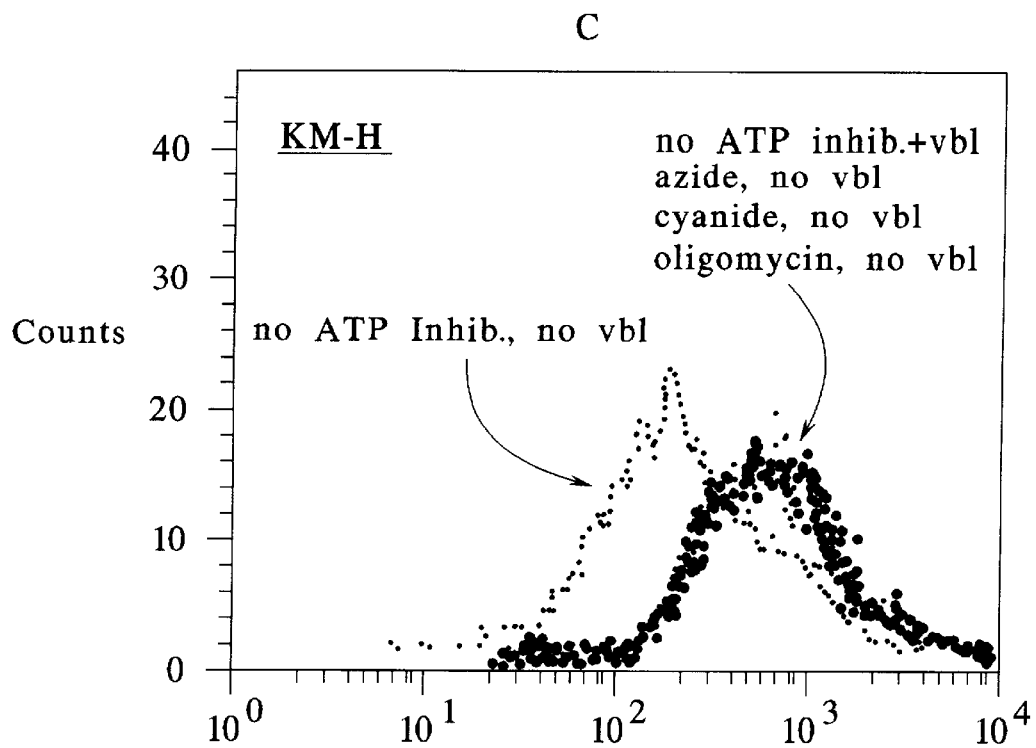
D
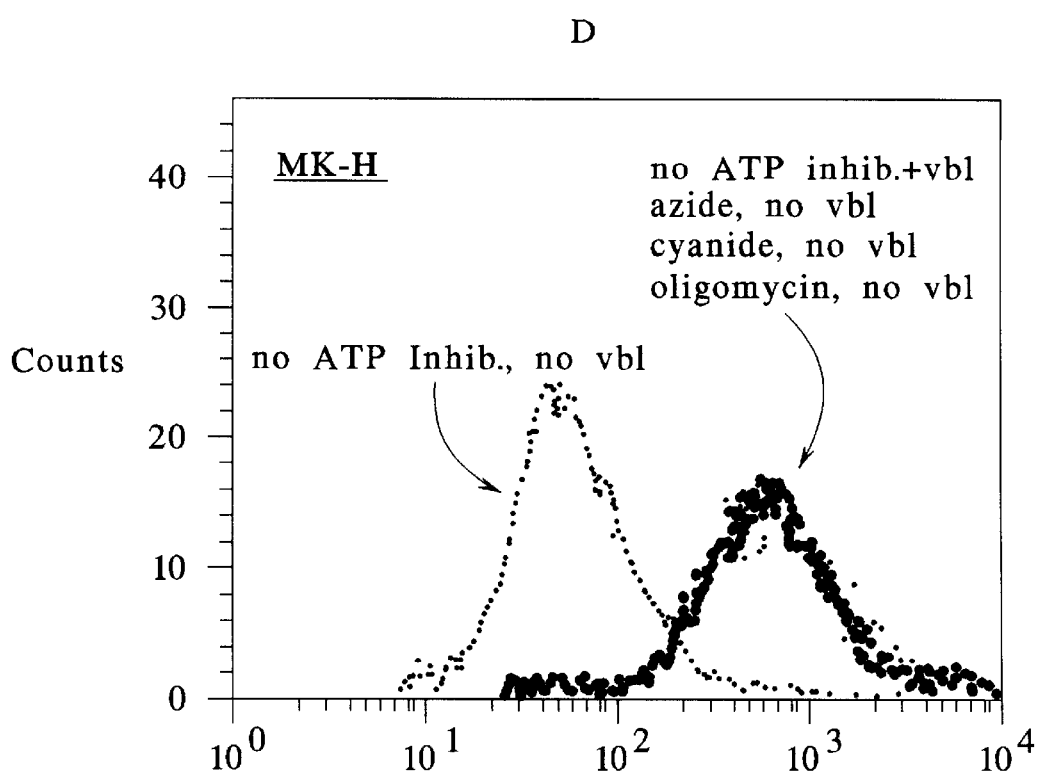

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 4669 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: 5'UTR
      (B) LOCATION: 1..424

(ix) FEATURE:
      (A) NAME/KEY: CDS
      (B) LOCATION: 425..4264

(ix) FEATURE:
      (A) NAME/KEY: 3'UTR
      (B) LOCATION: 4265..4669

(xi) SEQUENCE DESCRIPTION: SEQ ID NO: 1:

```
CCTACTCTAT TCAGATATTC TCCAGATTCC TAAAGATTAG AGATCATTTC TCATTCTCCT      60

AGGAGTACTC ACTTCAGGAA GCAACCAGAT AAAAGAGAGG TGCAACGGAA GCCAGAACAT     120

TCCTCCTGGA AATTCAACCT GTTTCGCAGT TTCTCGAGGA ATCAGCATTC AGTCAATCCG     180

GGCCGGGAGC AGTCATCTGT GGTGAGGCTG ATTGGCTGGG CAGGAACAGC GCCGGGGCGT     240

GGGCTGAGCG CAGCGCTTCG CTCTCTTTGC CACAGGAAGC CTGAGCTCAT TCGAGTAGCG     300

GCTCTTCCAA GCTCAAAGAA GCAGAGGCCG CTGTTCGTTT CCTTTAGGTC TTTCCACTAA     360

AGTCGGAGTA TCTTCTTCCA AGATTTCACG TCTTGGTGGC CGTTCCAAGG AGCGCGAGGT     420

CGGG ATG GAT CTT GAA GGG GAC CGC AAT GGA GGA GCA AAG AAG AAG AAC      469
     Met Asp Leu Glu Gly Asp Arg Asn Gly Gly Ala Lys Lys Lys Asn
      1               5                  10                  15

TTT TTT AAA CTG AAC AAT AAA AGT GAA AAA GAT AAG AAG GAA AAG AAA       517
Phe Phe Lys Leu Asn Asn Lys Ser Glu Lys Asp Lys Lys Glu Lys Lys
                 20                  25                  30

CCA ACT GTC AGT GTA TTT TCA ATG TTT CGC TAT TCA AAT TGG CTT GAC       565
Pro Thr Val Ser Val Phe Ser Met Phe Arg Tyr Ser Asn Trp Leu Asp
                 35                  40                  45

AAG TTG TAT ATG GTG GTG GGA ACT TTG GCT GCC ATC ATC CAT GGG GCT       613
Lys Leu Tyr Met Val Val Gly Thr Leu Ala Ala Ile Ile His Gly Ala
             50                  55                  60

GGA CTT CCT CTC ATG ATG CTG GTG TTT GGA GAA ATG ACA GAT ATC TTT       661
Gly Leu Pro Leu Met Met Leu Val Phe Gly Glu Met Thr Asp Ile Phe
     65                  70                  75

GCA AAT GCA GGA AAT TTA GAA GAT CTG ATG TCA AAC ATC ACT AAT AGA       709
Ala Asn Ala Gly Asn Leu Glu Asp Leu Met Ser Asn Ile Thr Asn Arg
 80                  85                  90                  95

AGT GAT ATC AAT GAT ACA GGG TTC TTC ATG AAT CTG GAG GAA GAC ATG       757
Ser Asp Ile Asn Asp Thr Gly Phe Phe Met Asn Leu Glu Glu Asp Met
                100                 105                 110

ACC AGG TAT GCC TAT TAT TAC AGT GGA ATT GGT GCT GGG GTG CTG GTT       805
Thr Arg Tyr Ala Tyr Tyr Tyr Ser Gly Ile Gly Ala Gly Val Leu Val
             115                 120                 125

GCT GCT TAC ATT CAG GTT TCA TTT TGG TGC CTG GCA GCT GGA AGA CAA       853
```

```
                 Ala Ala Tyr Ile Gln Val Ser Phe Trp Cys Leu Ala Ala Gly Arg Gln
                             130                 135                 140

ATA CAC AAA ATT AGA AAA CAG TTT TTT CAT GCT ATT ATG CGA CAG GAG              901
Ile His Lys Ile Arg Lys Gln Phe Phe His Ala Ile Met Arg Gln Glu
            145                 150                 155

ATA GGC TGG TTT GAT GTG CAC GAT GTT GGG GAG CTT AAC ACC CGA CTT              949
Ile Gly Trp Phe Asp Val His Asp Val Gly Glu Leu Asn Thr Arg Leu
160                 165                 170                 175

ACA GAT GAT GTC TCC AAG ATT AAT GAA GGA ATT GGT GAC AAA ATT GGA              997
Thr Asp Asp Val Ser Lys Ile Asn Glu Gly Ile Gly Asp Lys Ile Gly
                180                 185                 190

ATG TTC TTT CAG TCA ATG GCA ACA TTT TTC ACT GGG TTT ATA GTA GGA             1045
Met Phe Phe Gln Ser Met Ala Thr Phe Phe Thr Gly Phe Ile Val Gly
            195                 200                 205

TTT ACA CGT GGT TGG AAG CTA ACC CTT GTG ATT TTG GCC ATC AGT CCT             1093
Phe Thr Arg Gly Trp Lys Leu Thr Leu Val Ile Leu Ala Ile Ser Pro
        210                 215                 220

GTT CTT GGA CTG TCA GCT GCT GTC TGG GCA AAG ATA CTA TCT TCA TTT             1141
Val Leu Gly Leu Ser Ala Ala Val Trp Ala Lys Ile Leu Ser Ser Phe
        225                 230                 235

ACT GAT AAA GAA CTC TTA GCG TAT GCA AAA GCT GGA GCA GTA GCT GAA             1189
Thr Asp Lys Glu Leu Leu Ala Tyr Ala Lys Ala Gly Ala Val Ala Glu
240                 245                 250                 255

GAG GTC TTG GCA GCA ATT AGA ACT GTG ATT GCA TTT GGA GGA CAA AAG             1237
Glu Val Leu Ala Ala Ile Arg Thr Val Ile Ala Phe Gly Gly Gln Lys
                260                 265                 270

AAA GAA CTT GAA AGG TAC AAC AAA AAT TTA GAA GAA GCT AAA AGA ATT             1285
Lys Glu Leu Glu Arg Tyr Asn Lys Asn Leu Glu Glu Ala Lys Arg Ile
            275                 280                 285

GGG ATA AAG AAA GCT ATT ACA GCC AAT ATT TCT ATA GGT GCT GCT TTC             1333
Gly Ile Lys Lys Ala Ile Thr Ala Asn Ile Ser Ile Gly Ala Ala Phe
        290                 295                 300

CTG CTG ATC TAT GCA TCT TAT GCT GTG GCC TTC TGG TAT GGG ACC ACC             1381
Leu Leu Ile Tyr Ala Ser Tyr Ala Val Ala Phe Trp Tyr Gly Thr Thr
        305                 310                 315

TTG GTC CTC TCA GGG GAA TAT TCT ATT GGA CAA GTA CTC ACT GTA TTC             1429
Leu Val Leu Ser Gly Glu Tyr Ser Ile Gly Gln Val Leu Thr Val Phe
320                 325                 330                 335

TTT TCT GTA TTA ATT GGG GCT TTT AGT GTT GGA CAG GCA TCT CCA AGC             1477
Phe Ser Val Leu Ile Gly Ala Phe Ser Val Gly Gln Ala Ser Pro Ser
                340                 345                 350

ATT GAA GCA TTT GCA AAT GCA AGA GGA GCA GCT TAT GAA ATC TTC AAG             1525
Ile Glu Ala Phe Ala Asn Ala Arg Gly Ala Ala Tyr Glu Ile Phe Lys
            355                 360                 365

ATA ATT GAT AAT AAG CCA AGT ATT GAC AGC TAT TCG AAG AGT GGG CAC             1573
Ile Ile Asp Asn Lys Pro Ser Ile Asp Ser Tyr Ser Lys Ser Gly His
        370                 375                 380

AAA CCA GAT AAT ATT AAG GGA AAT TTG GAA TTC AGA AAT GTT CAC TTC             1621
Lys Pro Asp Asn Ile Lys Gly Asn Leu Glu Phe Arg Asn Val His Phe
385                 390                 395

AGT TAC CCA TCT CGA AAA GAA GTT AAG ATC TTG AAG GGC CTG AAC CTG             1669
Ser Tyr Pro Ser Arg Lys Glu Val Lys Ile Leu Lys Gly Leu Asn Leu
400                 405                 410                 415

AAG GTG CAG AGT GGG CAG ACG GTG GCC CTG GTT GGA AAC AGT GGC TGT             1717
Lys Val Gln Ser Gly Gln Thr Val Ala Leu Val Gly Asn Ser Gly Cys
                420                 425                 430

GGG AAG AGC ACA ACA GTC CAG CTG ATG CAG AGG CTC TAT GAC CCC ACA             1765
Gly Lys Ser Thr Thr Val Gln Leu Met Gln Arg Leu Tyr Asp Pro Thr
            435                 440                 445
```

```
GAG GGG ATG GTC AGT GTT GAT GGA CAG GAT ATT AGG ACC ATA AAT GTA          1813
Glu Gly Met Val Ser Val Asp Gly Gln Asp Ile Arg Thr Ile Asn Val
            450                 455                 460

AGG TTT CTA CGG GAA ATC ATT GGT GTG GTG AGT CAG GAA CCT GTA TTG          1861
Arg Phe Leu Arg Glu Ile Ile Gly Val Val Ser Gln Glu Pro Val Leu
465                 470                 475

TTT GCC ACC ACG ATA GCT GAA AAC ATT CGC TAT GGC CGT GAA AAT GTC          1909
Phe Ala Thr Thr Ile Ala Glu Asn Ile Arg Tyr Gly Arg Glu Asn Val
480                 485                 490                 495

ACC ATG GAT GAG ATT GAG AAA GCT GTC AAG GAA GCC AAT GCC TAT GAC          1957
Thr Met Asp Glu Ile Glu Lys Ala Val Lys Glu Ala Asn Ala Tyr Asp
                500                 505                 510

TTT ATC ATG AAA CTG CCT CAT AAA TTT GAC ACC CTG GTT GGA GAG AGA          2005
Phe Ile Met Lys Leu Pro His Lys Phe Asp Thr Leu Val Gly Glu Arg
            515                 520                 525

GGG GCC CAG TTG AGT GGT GGG CAG AAG CAG AGG ATC GCC ATT GCA CGT          2053
Gly Ala Gln Leu Ser Gly Gly Gln Lys Gln Arg Ile Ala Ile Ala Arg
            530                 535                 540

GCC CTG GTT CGC AAC CCC AAG ATC CTC CTG CTG GAT GAG GCC ACG TCA          2101
Ala Leu Val Arg Asn Pro Lys Ile Leu Leu Leu Asp Glu Ala Thr Ser
545                 550                 555

GCC TTG GAC ACA GAA AGC GAA GCA GTG GTT CAG GTG GCT CTG GAT AAG          2149
Ala Leu Asp Thr Glu Ser Glu Ala Val Val Gln Val Ala Leu Asp Lys
560                 565                 570                 575

GCC AGA AAA GGT CGG ACC ACC ATT GTG ATA GCT CAT CGT TTT GCT ACA          2197
Ala Arg Lys Gly Arg Thr Thr Ile Val Ile Ala His Arg Phe Ala Thr
                580                 585                 590

GTT CGT AAT GCT GAC GTC ATC GCT GGT TTC GAT GAT GGA GTC ATT GTG          2245
Val Arg Asn Ala Asp Val Ile Ala Gly Phe Asp Asp Gly Val Ile Val
            595                 600                 605

GAG AAA GGA AAT CAT GAT GAA CTC ATG AAA GAG AAA GGC ATT TAC TTC          2293
Glu Lys Gly Asn His Asp Glu Leu Met Lys Glu Lys Gly Ile Tyr Phe
            610                 615                 620

AAA CTT GTC ACA ATG CAG ACA GCA GGA AAT GAA GTT GAA TTA GAA AAT          2341
Lys Leu Val Thr Met Gln Thr Ala Gly Asn Glu Val Glu Leu Glu Asn
625                 630                 635

GCA GCT GAT GAA TCC AAA AGT GAA ATT GAT GCC TTG GAA ATG TCT TCA          2389
Ala Ala Asp Glu Ser Lys Ser Glu Ile Asp Ala Leu Glu Met Ser Ser
640                 645                 650                 655

AAT GAT TCA AGA TCC AGT CTA ATA AGA AAA AGA TCA ACT CGT AGG AGT          2437
Asn Asp Ser Arg Ser Ser Leu Ile Arg Lys Arg Ser Thr Arg Arg Ser
                660                 665                 670

GTC CGT GGA TCA CAA GCC CAA CAC AGA AAG CTT AGT ACC AAA GAG GCT          2485
Val Arg Gly Ser Gln Ala Gln His Arg Lys Leu Ser Thr Lys Glu Ala
            675                 680                 685

CTG GAT GAA AGT ATA CCT CCA GTT TCC TTT TGG AGG ATT ATG AAG CTA          2533
Leu Asp Glu Ser Ile Pro Pro Val Ser Phe Trp Arg Ile Met Lys Leu
            690                 695                 700

AAT TTA ACT GAA TGG CCT TAT TTT GTT GTT GGT GTA TTT TGT GCC ATT          2581
Asn Leu Thr Glu Trp Pro Tyr Phe Val Val Gly Val Phe Cys Ala Ile
705                 710                 715

ATA AAT GGA GGC CTG CAA CCA GCA TTT GCA ATA ATA TTT TCA AAG ATT          2629
Ile Asn Gly Gly Leu Gln Pro Ala Phe Ala Ile Ile Phe Ser Lys Ile
720                 725                 730                 735

ATA GGG GTT TTT ACA AGA ATT GAT GAT CCT GAA ACA AAA CGA CAG AAT          2677
Ile Gly Val Phe Thr Arg Ile Asp Asp Pro Glu Thr Lys Arg Gln Asn
                740                 745                 750

AGT AAC TTG TTT TCA CTA TTG TTT CTA GCC CTT GGA ATT ATT TCT TTT          2725
Ser Asn Leu Phe Ser Leu Leu Phe Leu Ala Leu Gly Ile Ile Ser Phe
            755                 760                 765
```

```
ATT ACA TTT TTC CTT CAG GGT TTC ACA TTT GGC AAA GCT GGA GAG ATC    2773
Ile Thr Phe Phe Leu Gln Gly Phe Thr Phe Gly Lys Ala Gly Glu Ile
        770                 775                 780

CTC ACC AAG CGG CTC CGA TAC ATG GTT TTC CGA TCC ATG CTC AGA CAG    2821
Leu Thr Lys Arg Leu Arg Tyr Met Val Phe Arg Ser Met Leu Arg Gln
    785                 790                 795

GAT GTG AGT TGG TTT CAT GAC CCT AAA AAC ACC ACT GGA GCA TTG ACT    2869
Asp Val Ser Trp Phe His Asp Pro Lys Asn Thr Thr Gly Ala Leu Thr
800                 805                 810                 815

ACC AGG CTC GCC AAT GAT GCT GCT CAA GTT AAA GGG GCT ATA GGT TCC    2917
Thr Arg Leu Ala Asn Asp Ala Ala Gln Val Lys Gly Ala Ile Gly Ser
            820                 825                 830

AGG CTT GCT GTA ATT ACC CAG AAT ATA GCA AAT CTT GGG ACA GGA ATA    2965
Arg Leu Ala Val Ile Thr Gln Asn Ile Ala Asn Leu Gly Thr Gly Ile
        835                 840                 845

ATT ATA TCC TTC ATC TAT GGT TGG CAA CTA ACA CTG TTA CTC TTA GCA    3013
Ile Ile Ser Phe Ile Tyr Gly Trp Gln Leu Thr Leu Leu Leu Leu Ala
        850                 855                 860

ATT GTA CCC ATC ATT GCA ATA GCA GGA GTT GTT GAA ATG AAA ATG TTT    3061
Ile Val Pro Ile Ile Ala Ile Ala Gly Val Val Glu Met Lys Met Phe
    865                 870                 875

GCT GGA CAA GCA CTG AAA GAT AAG AAA GAA CTA GAA GGT GCT GGG AAG    3109
Ala Gly Gln Ala Leu Lys Asp Lys Lys Glu Leu Glu Gly Ala Gly Lys
880                 885                 890                 895

ATC GCT ACT GAA GCA ATA GAA AAC TTC CGA ACC GTT GTT TCT TTG ACT    3157
Ile Ala Thr Glu Ala Ile Glu Asn Phe Arg Thr Val Val Ser Leu Thr
            900                 905                 910

CAG GAG CAG AAG TTT GAA CAT ATG TAT GCT CAG AGT TTG CAG GTA CCA    3205
Gln Glu Gln Lys Phe Glu His Met Tyr Ala Gln Ser Leu Gln Val Pro
        915                 920                 925

TAC AGA AAC TCT TTG AGG AAA GCA CAC ATC TTT GGA ATT ACA TTT TCC    3253
Tyr Arg Asn Ser Leu Arg Lys Ala His Ile Phe Gly Ile Thr Phe Ser
        930                 935                 940

TTC ACC CAG GCA ATG ATG TAT TTT TCC TAT GCT GGA TGT TTC CGG TTT    3301
Phe Thr Gln Ala Met Met Tyr Phe Ser Tyr Ala Gly Cys Phe Arg Phe
    945                 950                 955

GGA GCC TAC TTG GTG GCA CAT AAA CTC ATG AGC TTT GAG GAT GTT CTG    3349
Gly Ala Tyr Leu Val Ala His Lys Leu Met Ser Phe Glu Asp Val Leu
960                 965                 970                 975

TTA GTA TTT TCA GCT GTT GTC TTT GGT GCC ATG GCC GTG GGG CAA GTC    3397
Leu Val Phe Ser Ala Val Val Phe Gly Ala Met Ala Val Gly Gln Val
            980                 985                 990

AGT TCA TTT GCT CCT GAC TAT GCC AAA GCC AAA ATA TCA GCA GCC CAC    3445
Ser Ser Phe Ala Pro Asp Tyr Ala Lys Ala Lys Ile Ser Ala Ala His
        995                 1000                1005

ATC ATC ATG ATC ATT GAA AAA ACC CCT TTG ATT GAC AGC TAC AGC ACG    3493
Ile Ile Met Ile Ile Glu Lys Thr Pro Leu Ile Asp Ser Tyr Ser Thr
        1010                1015                1020

GAA GGC CTA ATG CCG AAC ACA TTG GAA GGA AAT GTC ACA TTT GGT GAA    3541
Glu Gly Leu Met Pro Asn Thr Leu Glu Gly Asn Val Thr Phe Gly Glu
    1025                1030                1035

GTT GTA TTC AAC TAT CCC ACC CGA CCG GAC ATC CCA GTG CTT CAG GGA    3589
Val Val Phe Asn Tyr Pro Thr Arg Pro Asp Ile Pro Val Leu Gln Gly
1040                1045                1050                1055

CTG AGC CTG GAG GTG AAG AAG GGC CAG ACG CTG GCT CTG GTG GGC AGC    3637
Leu Ser Leu Glu Val Lys Lys Gly Gln Thr Leu Ala Leu Val Gly Ser
            1060                1065                1070

AGT GGC TGT GGG AAG AGC ACA GTG GTC CAG CTC CTG GAG CGG TTC TAC    3685
Ser Gly Cys Gly Lys Ser Thr Val Val Gln Leu Leu Glu Arg Phe Tyr
```

```
                1075              1080              1085
GAC CCC TTG GCA GGG AAA GTG CTG CTT GAT GGC AAA GAA ATA AAG CGA      3733
Asp Pro Leu Ala Gly Lys Val Leu Leu Asp Gly Lys Glu Ile Lys Arg
        1090              1095              1100

CTG AAT GTT CAG TGG CTC CGA GCA CAC CTG GGC ATC GTG TCC CAG GAG      3781
Leu Asn Val Gln Trp Leu Arg Ala His Leu Gly Ile Val Ser Gln Glu
    1105              1110              1115

CCC ATC CTG TTT GAC TGC AGC ATT GCT GAG AAC ATT GCC TAT GGA GAC      3829
Pro Ile Leu Phe Asp Cys Ser Ile Ala Glu Asn Ile Ala Tyr Gly Asp
1120              1125              1130              1135

AAC AGC CGG GTG GTG TCA CAG GAA GAG ATC GTG AGG GCA GCA AAG GAG      3877
Asn Ser Arg Val Val Ser Gln Glu Glu Ile Val Arg Ala Ala Lys Glu
            1140              1145              1150

GCC AAC ATA CAT GCC TTC ATC GAG TCA CTG CCT AAT AAA TAT AGC ACT      3925
Ala Asn Ile His Ala Phe Ile Glu Ser Leu Pro Asn Lys Tyr Ser Thr
        1155              1160              1165

AAA GTA GGA GAC AAA GGA ACT CAG CTC TCT GGT GGC CAG AAA CAA CGC      3973
Lys Val Gly Asp Lys Gly Thr Gln Leu Ser Gly Gly Gln Lys Gln Arg
    1170              1175              1180

ATT GCC ATA GCT CGT CGC CTT GTT AGA CAG CCT CAT ATT TTG CTT TTG      4021
Ile Ala Ile Ala Arg Arg Leu Val Arg Gln Pro His Ile Leu Leu Leu
        1185              1190              1195

GAT GAA GCC ACG TCA GCT CTG GAT ACA GAA AGT GAA AAG GTT GTC CAA      4069
Asp Glu Ala Thr Ser Ala Leu Asp Thr Glu Ser Glu Lys Val Val Gln
1200              1205              1210              1215

GAA GCC CTG GAC AAA GCC AGA GAA GGC CGC ACC TGC ATT GTG ATT GCT      4117
Glu Ala Leu Asp Lys Ala Arg Glu Gly Arg Thr Cys Ile Val Ile Ala
            1220              1225              1230

CAC CGC CTG TCC ACC ATC CAG AAT GCA GAC TTA ATA GTG GTG TTT CAG      4165
His Arg Leu Ser Thr Ile Gln Asn Ala Asp Leu Ile Val Val Phe Gln
        1235              1240              1245

AAT GGC AGA GTC AAG GAG CAT GGC ACG CAT CAG CAG CTG CTG GCA CAG      4213
Asn Gly Arg Val Lys Glu His Gly Thr His Gln Gln Leu Leu Ala Gln
    1250              1255              1260

AAA GGC ATC TAT TTT TCA ATG GTC AGT GTC CAG GCT GGA ACA AAG CGC      4261
Lys Gly Ile Tyr Phe Ser Met Val Ser Val Gln Ala Gly Thr Lys Arg
        1265              1270              1275

CAG TGAACTCTGA CTGTATGAGA TGTTAAATAC TTTTTAATAT TTGTTTAGAT           4314
Gln
1280

ATGACATTTA TTCAAAGTTA AAAGCAAACA CTTACAGAAT TATGAAGAGG TATCTGTTTA    4374

ACATTTCCTC AGTCAAGTTC AGAGTCTTCA GAGACTTCGT AATTAAAGGA ACAGAGTGAG    4434

AGACATCATC AAGTGGAGAG AAATCATAGT TTAAACTGCA TTATAAATTT TATAACAGAA    4494

TTAAAGTAGA TTTTAAAAGA TAAAATGTGT AATTTTGTTT ATATTTTCCC ATTTGGACTG    4554

TAACTGACTG CCTTGCTAAA AGATTATAGA AGTAGCAAAA AGTATTGAAA TGTTTGCATA    4614

AAGTGTCTAT AATAAAACTA AACTTTCATG TGAAAAAAAA AAAAAAAAAA AAAAA         4669

(2) INFORMATION FOR SEQ ID NO: 2:

(i) SEQUENCE CHARACTERISTICS:
        (A) LENGTH: 1280 amino acids
        (B) TYPE: amino acid
        (D) TOPOLOGY: linear (ii) MOLECULE TYPE: protein (xi) SEQUENCE DESCRIPTION: SEQ ID NO: 2:

Met Asp Leu Glu Gly Asp Arg Asn Gly Gly Ala Lys Lys Lys Asn Phe
```

-continued

```
  1               5                  10                 15
Phe Lys Leu Asn Asn Lys Ser Glu Lys Asp Lys Lys Glu Lys Lys Pro
            20                  25                 30

Thr Val Ser Val Phe Ser Met Phe Arg Tyr Ser Asn Trp Leu Asp Lys
            35                  40                 45

Leu Tyr Met Val Val Gly Thr Leu Ala Ala Ile Ile His Gly Ala Gly
 50                      55                  60

Leu Pro Leu Met Met Leu Val Phe Gly Glu Met Thr Asp Ile Phe Ala
 65                  70                  75                  80

Asn Ala Gly Asn Leu Glu Asp Leu Met Ser Asn Ile Thr Asn Arg Ser
                 85                  90                  95

Asp Ile Asn Asp Thr Gly Phe Phe Met Asn Leu Glu Glu Asp Met Thr
                100                 105                110

Arg Tyr Ala Tyr Tyr Ser Gly Ile Gly Ala Gly Val Leu Val Ala
            115                 120                 125

Ala Tyr Ile Gln Val Ser Phe Trp Cys Leu Ala Ala Gly Arg Gln Ile
            130                 135                 140

His Lys Ile Arg Lys Gln Phe His Ala Ile Met Arg Gln Glu Ile
145             150                 155                 160

Gly Trp Phe Asp Val His Asp Val Gly Glu Leu Asn Thr Arg Leu Thr
                    165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
            195                 200                 205

Thr Arg Gly Trp Lys Leu Thr Leu Val Ile Leu Ala Ile Ser Pro Val
 210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
            275                 280                 285

Ile Lys Lys Ala Ile Thr Ala Asn Ile Ser Ile Gly Ala Ala Phe Leu
290                 295                 300

Leu Ile Tyr Ala Ser Tyr Ala Val Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
            355                 360                 365

Ile Asp Asn Lys Pro Ser Ile Asp Ser Tyr Ser Lys Ser Gly His Lys
            370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430
```

-continued

```
Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
        450                 455                 460

Phe Leu Arg Glu Ile Ile Gly Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
        530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Phe Ala Thr Val
                580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
        610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln His Arg Lys Leu Ser Thr Lys Glu Ala Leu
        675                 680                 685

Asp Glu Ser Ile Pro Pro Val Ser Phe Trp Arg Ile Met Lys Leu Asn
        690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu
        770                 775                 780

Thr Lys Arg Leu Arg Tyr Met Val Phe Arg Ser Met Leu Arg Gln Asp
785                 790                 795                 800

Val Ser Trp Phe His Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
        835                 840                 845
```

-continued

```
Ile Ser Phe Ile Tyr Gly Trp Gln Leu Thr Leu Leu Leu Ala Ile
    850                 855                 860
Val Pro Ile Ile Ala Ile Ala Gly Val Val Glu Met Lys Met Phe Ala
865                 870                 875                 880
Gly Gln Ala Leu Lys Asp Lys Lys Glu Leu Glu Gly Ala Gly Lys Ile
                885                 890                 895
Ala Thr Glu Ala Ile Glu Asn Phe Arg Thr Val Val Ser Leu Thr Gln
            900                 905                 910
Glu Gln Lys Phe Glu His Met Tyr Ala Gln Ser Leu Gln Val Pro Tyr
        915                 920                 925
Arg Asn Ser Leu Arg Lys Ala His Ile Phe Gly Ile Thr Phe Ser Phe
    930                 935                 940
Thr Gln Ala Met Met Tyr Phe Ser Tyr Ala Gly Cys Phe Arg Phe Gly
945                 950                 955                 960
Ala Tyr Leu Val Ala His Lys Leu Met Ser Phe Glu Asp Val Leu Leu
                965                 970                 975
Val Phe Ser Ala Val Val Phe Gly Ala Met Ala Val Gly Gln Val Ser
            980                 985                 990
Ser Phe Ala Pro Asp Tyr Ala Lys Ala Lys Ile Ser Ala Ala His Ile
        995                 1000                1005
Ile Met Ile Ile Glu Lys Thr Pro Leu Ile Asp Ser Tyr Ser Thr Glu
    1010                1015                1020
Gly Leu Met Pro Asn Thr Leu Glu Gly Asn Val Thr Phe Gly Glu Val
1025                1030                1035                1040
Val Phe Asn Tyr Pro Thr Arg Pro Asp Ile Pro Val Leu Gln Gly Leu
                1045                1050                1055
Ser Leu Glu Val Lys Lys Gly Gln Thr Leu Ala Leu Val Gly Ser Ser
            1060                1065                1070
Gly Cys Gly Lys Ser Thr Val Val Gln Leu Leu Glu Arg Phe Tyr Asp
        1075                1080                1085
Pro Leu Ala Gly Lys Val Leu Leu Asp Gly Lys Glu Ile Lys Arg Leu
    1090                1095                1100
Asn Val Gln Trp Leu Arg Ala His Leu Gly Ile Val Ser Gln Glu Pro
1105                1110                1115                1120
Ile Leu Phe Asp Cys Ser Ile Ala Glu Asn Ile Ala Tyr Gly Asp Asn
                1125                1130                1135
Ser Arg Val Val Ser Gln Glu Glu Ile Val Arg Ala Ala Lys Glu Ala
            1140                1145                1150
Asn Ile His Ala Phe Ile Glu Ser Leu Pro Asn Lys Tyr Ser Thr Lys
        1155                1160                1165
Val Gly Asp Lys Gly Thr Gln Leu Ser Gly Gly Gln Lys Gln Arg Ile
    1170                1175                1180
Ala Ile Ala Arg Arg Leu Val Arg Gln Pro His Ile Leu Leu Leu Asp
1185                1190                1195                1200
Glu Ala Thr Ser Ala Leu Asp Thr Glu Ser Glu Lys Val Val Gln Glu
                1205                1210                1215
Ala Leu Asp Lys Ala Arg Glu Gly Arg Thr Cys Ile Val Ile Ala His
            1220                1225                1230
Arg Leu Ser Thr Ile Gln Asn Ala Asp Leu Ile Val Val Phe Gln Asn
        1235                1240                1245
Gly Arg Val Lys Glu His Gly Thr His Gln Gln Leu Leu Ala Gln Lys
    1250                1255                1260
```

-continued

```
Gly Ile Tyr Phe Ser Met Val Ser Val Gln Ala Gly Thr Lys Arg Gln
1265                1270                1275                1280
```

METHODS AND REAGENTS FOR PREPARING AND USING IMMUNOLOGICAL AGENTS SPECIFIC FOR P-GLYCOPROTEIN

This application is a divisional of U.S. patent application Ser. No. 08/752,447, filed Nov. 15, 1996 now U.S. Pat. No. 5,994,088.

This invention was made with government support under grant CAR-3740333 by the National Cancer Institute/National Institutes of Health. The government has certain rights in the invention.

BACKGROUND OF THE INVENTION

1. Field of the Invention

The present invention relates to the use of immunological reagents specific for a human transmembrane efflux pump protein (P-glycoprotein) in a biochemical conformation adopted in the presence of certain cytotoxic, lipophilic drugs that are substrates for P-glycoprotein, in the presence of cellular ATP depleting agents, and by certain mutant embodiments of Pgp. The invention provides such immunological reagents for immunodiagnostic and therapeutic uses, for isolating lymphocytes and hematopoietic stem cells, and for anticancer drug development.

2. Background of the Invention

Many human cancers express intrinsically or develop spontaneously resistance to several classes of anticancer drugs, each with a different structure and different mechanism of action. This phenomenon, which can be mimicked in cultured mammalian cells selected for resistance to certain A plant alkaloids or antitumor antibiotics such as colchicine, vinblastine and doxorubicin (formerly known as Adriamycin), is generally referred to as multidrug resistance ("MDR"; see Roninson (ed.), 1991, *Molecular and Cellular Biology of Multidrug Resistance in Tumor Cells*, Plenum Press, N.Y., 1991; Gottesman et al., 1991, in *Biochemical Bases for Multidrug Resistance in Cancer*, Academic Press, N.Y., Chapter 11 for reviews). The MDR phenotype presents a major obstacle to successful cancer chemotherapy in human patients.

MDR frequently appears to result from decreased intracellular accumulation of drug as a consequence of increased drug efflux related to alterations at the cellular plasma membrane. When mutant cell lines having the MDR phenotype are isolated, they are found to express an ATP-dependent non-specific molecular "pump" protein (generally known as P-glycoprotein) that is located in the plasma membrane and keeps the intracellular accumulation of an anti-cancer drug low enough to evoke the drug-resistance phenotype. This protein (which has been determined to be the gene product of the MDR1 gene in humans) facilitates active (i.e., energy-dependent) drug efflux from the cell, against a concentration gradient of (generally) lipophilic compounds, including many cytotoxic drugs.

The gene encoding P-glycoprotein (which is also known as gp170–180 and the multidrug transporter) has been cloned from cultured human cells by Roninson et al. (see co-owned U.S. Pat. No. 5,206,352, issued Apr. 27, 1993, having an effective filing date of Mar. 28, 1986), and is generally referred to as MDR 1. The protein product of the MDR 1 gene, most generally known as P-glycoprotein ("Pgp"), is a 170–180 kilodalton (kDa) transmembrane protein having the aforementioned energy-dependent efflux pump activity.

Molecular analysis of the MDR1 gene indicates that Pgp consists of 1280 amino acids distributed between two homologous halves (having 43% sequence identity of amino acid residues), each half of the molecule comprising six hydrophobic transmembrane domains and an ATP binding site within a cytoplasmic loop. Only about 8% of the molecule is extracellular, and carbohydrate moieties (approximately 30 kDa) are bound to sites in this region (Chen et al., 1986, *Cell* 47: 381–387).

Expression of Pgp on the cell surface is sufficient to render cells resistant to many (but not all) cytotoxic drugs, including many anti-cancer agents. Pgp-mediated MDR appears to be an important clinical component of drug resistance in tumors of different types, and MDR1 gene expression correlates with resistance to chemotherapy in different types of cancer.

Because Pgp is involved in the resistance of different types of human malignancies to conventional chemotherapy, the expression of Pgp is an important diagnostic and prognostic factor which in many cases helps the physician to choose the most effective combination of chemotherapeutic drugs and to monitor the efficacy of treatment. One way Pgp expression has been evaluated is by detecting the binding of specific immunological reagents (antibodies) to tumor samples. However, frequently the expression level of Pgp in tumor cells is low and cannot be reproducibly detected by routine immunological methods. In addition, there are few immunological or other reagents specific for functionally-active Pgp (which are the only forms of Pgp that are clinically relevant). Thus, there is a need in the art to increase the sensitivity and specificity of immunological and immunohistochemical methods for detecting functional Pgp expression.

Pgp is also constitutively expressed in many normal cells and tissues (see Cordon-Cardo et al., 1990, *J. Histochem. Cytochem.* 3: 1277; and Thiebaut et al., 1987, *Proc. Natl. Acad. Sci. USA* 84: 7735 for reviews). In hematopoietic cells, Neyfakh et al. (1989, *Exp. Cancer Res.* 185–496) have shown that certain subsets of human and murine lymphocytes efflux Rh123, a fluorescent dye that is a Pgp substrate, and this process can be blocked by small molecule inhibitors of Pgp. It has been demonstrated more recently that Pgp is expressed on the cell-surface membranes of pluripotent stem cells, NK cells, CD4- and CD8-positive T lymphocytes, and B lymphocytes (Chaudhary et al., 1992, *Blood* 8: 2735; Drach et al., 1992, *Blood* 80: 2729; Kimecki et al., 1994, *Blood* 83: 2451; Chaudhary et al., 1991, *Cell* 66: 85). Pgp expression on the cell surface membranes of different subsets of human lymphocytes has been extensively documented (Coon et al., 1991, *Human Immunol.* 32: 134; Tiirikainen et al., 1992, *Ann. Hematol.* 65: 124; Schluesener et al., 1992, *Immunopharmacology* 23: 37; Gupta et al., 1993, *J. Clin. Immunol.* 13: 289). Although recent studies suggest that Pgp plays a role in normal physiological functions of immune cells (Witkowski et al., 1994, *J. Immunol.* 153: 658; Kobayashi et al., 1994, *Biochem. Pharmacol.* 48: 1641; Raghu et al., 1996, *Exp. Hematol.* 24: 1030–1036, as disclosed more fully in co-pending U.S. patent application Ser. No. 08/658,583, filed Jun. 7, 1996, incorporated by reference herein in its entirety), the physiological role of Pgp in normal immune cells has remained unclear to date.

Expression of Pgp in hematopoietic cells provides an effective means for identifying and purifying lymphocytes and hematopoietic stem cells. As described more completely in co-owned and/or co-pending U.S. Pat. No. 5,434,075, issued Jul. 18, 1995 and U.S. patent application Ser. No. 08/032,056, filed Mar. 16, 1993, functional Pgp assays (such as fluorescent dye efflux) and immunochemical methods (such as fluorescence activated cell sorting (FACS) analysis)

can in theory be used to purify lymphocytes and hematopoietic stem cells.

However, the levels of expression of Pgp on stem cells are low, and consequently the amount of an immunological reagent such as a monoclonal antibody (mAb) bound to a hematopoietic stem cell membrane using conventional procedures is generally not high enough to efficiently separate Pgp-positive cells by any conventional immunological technique (such as FACS, immunomagnetic particle separation, cell panning, or other methods known in the art). Thus, there remains a need in this art to improve the efficiency of methods for using Pgp expression to specifically purify lymphocytes and hematopoietic stem cells from biological sources.

Once the central role in MDR played by Pgp was uncovered, agents with a potential for reversing MDR phenotypes were developed that target Pgp. Several classes of drugs, including calcium channel blockers (e.g., verapamil), immunosuppresants (such as cyclosporines and steroid hormones), calmodulin inhibitors, and other compounds, were found to enhance the intracellular accumulation and cytotoxic action of Pgp-transported drugs (Ford et al., 1990, *Pharm. Rev.* 42: 155). Many of these agents were found to inhibit either drug binding or drug transport by Pgp (Akiyama et al., 1988, *Molec. Pharm.* 3: 144; Horio et al., 1988, *Proc. Natl. Acad. Sci. USA* 84: 3580). Some of these agents themselves were found to bind to and be effluxed by Pgp, suggesting that their enhancing effects on the cytotoxicity of Pgp substrates are due, at least in part, to competition for drug binding sites on this protein (Cornwell et al., 1986, *J. Bio. Chem.* 261: 7921; Tamai, 1990, *J. Biochem. Molec. Biol.* 265: 16509).

Many of these agents, however, also have strong, deleterious side effects at physiologically-achievable concentrations. These systemic side effects severely limit the clinical use of these agents as specific inhibitors of Pgp or for negative selection against Pgp-expressing tumor cells. Most of the known MDR-reversing drugs used in clinical trials have major side effects unrelated to inhibition of Pgp, such as calcium channel blockage (verapamil) or immunosuppression (cyclosporines and steroids). Similarly, targeting of cytotoxic drugs to Pgp-expressing cells is capable of compromising normal tissue function in normal cells (such as kidney, liver, colonic epithelium, etc.) that normally express Pgp. These drawbacks restrict the clinically-achievable dose of such agents and ultimately, their usefulness.

Immunological reagents, specifically such agents linked to cytotoxic molecules or detectably labeled reporter molecules, provide an alternate and specific way for identifying cells expressing Pgp at the cell surface and specifically delivering cytotoxic substances directly to such cells. Immunological reagents specific for extracellular epitopes of Pgp, such as anti-Pgp antibodies, offered the prospect of specificity, since antibodies should target only Pgp. However, it has also been recognized that only antibodies which react with an extracellular epitope of Pgp are expected to react with the protein in the plasma membrane of intact cells and thereby inhibit the MDR phenotype in such cells. Antibodies directed to the cytoplasmic portion of Pgp, on the other hand, are unlikely to be useful for reversal of MDR.

In addition, antibody binding to Pgp was expected to have a more-prolonged inhibitory effect than that caused by transient binding of a competitive inhibitor. Such reagents may also provide a means for delivering cytotoxic agents specifically to Pgp-expressing tumor cells in regimens aimed to selective killing of such cells.

Monoclonal antibodies specific for Pgp are known in the art.

Hamada et al., 1986, *Proc. Natl. Acad. Sci. USA* 83: 7785 disclose the mAbs MRK-16 and MRK-17, produced by immunizing mice with doxorubicin-resistant K-562 human leukemia cells. MRK-16 mAb was also reported to modulate vincristine and actinomycin D transport in resistant cells, and MRK-17 was shown to specifically inhibit growth of resistant cells with these drugs. Meyers et al., 1987, *Cancer Res.* 49: 3209 disclose mAbs HYB-241 and HYB-612, which recognize an external epitope of Pgp.

O'Brien et al., 1989, *Proc. Amer. Assoc. Cancer Res.* 30:Abs 2114 disclose that mAbs HYB-241 and HYB-612 increased the accumulation of vincristine and actinomycin D in tumor cells and increased the cytotoxicity of combinations of these drugs with verapamil.

Tsuruo et al., 1989, *Jpn. J. Cancer Res.* 80: 627 reported that treatment of athymic mice that had been previously inoculated with drug resistant human ovarian cancer cells with the mAb MRK 16 caused regression of established subcutaneous tumors.

Hamada et al., 1990, *Cancer Res.* 50: 3167 disclosed a recombinant chimeric antibody that combines the variable region of MRK-16 with the $F_c$ portion of a human antibody, and showed this chimeric antibody to be more effective than MRK-16 mAb in increasing cytotoxicity in vitro.

Pearson et al., 1991, *J. Natl. Cancer Inst.* 88: 1386 disclosed that MRK-16 mAb increased the in vivo toxicity of vincristine to a human MDR colon cancer cell line grown as a xenograft in nude mice. The in vitro potentiation of drug cytotoxicity by MRK-16 mAb was, however, weak relative to known chemical inhibitors of Pgp action, and was apparently limited to only two Pgp substrates (vincristine and actinomycin D), having no effect on cytotoxicity by doxorubicin.

Cinciarelli et al., 1991, *Int. J. Cancer* 47: 533 disclosed a mouse IgG2, mAb, termed MAb657, having cross reactivity to Pgp-expressing human MDR cells. This mAb was shown to increase the susceptibility of MDR cells to human peripheral blood lymphocyte-mediated cytotoxicity, but was not shown to have an inhibitory effect on the drug efflux activity of Pgp.

Arcesi et al., 1993, *Cancer Res.* 53: 310–317 disclosed mAb 4E3 that binds to extracellular epitopes of Pgp but does not disrupt drug efflux or potentiate MDR drug-induced cytotoxicity.

Mechetner and Roninson, in co-owned and/or co-pending U.S. Pat. No. 5,434,075, issued Jul. 18, 1995, and in U.S. patent application Ser. No. 08/032,056, filed Mar. 16, 1993, disclosed mAb UIC2, having specificity for extracellular Pgp epitopes. This antibody was also shown to effectively inhibit Pgp-mediated drug efflux in MDR cells, and to reverse the MDR phenotype in vitro thereby, for a number of structurally and functional different cytotoxic compounds and all tested chemotherapeutic drugs known to be substrates for Pgp-mediated drug efflux.

The production of UIC2 mAb demonstrated the usefulness of the development of mAbs specific for extracellular epitopes of Pgp that were capable of inhibiting drug efflux activity. As evidenced by the mAbs developed in the prior art, production of extracellular epitope-specific mAbs does not necessarily result in mAbs that can affect drug efflux. There thus remains in the art a need for developing methods for producing mAbs that are capable of inhibiting drug efflux activity in Pgp. There also remains a need in the art for methods for developing more sensitive mAbs and methods to improve the sensitivity of currently available mAbs for the detection of Pgp expression in cancer cells in vivo, for improved cancer diagnostics and therapeutic applications with both normal and tumor cells expressing Pgp. There also remains a need in the art to develop more specific and efficient tools for the isolation of lymphocytes and hematopoietic stem cells, especially pluripotent and totipotent stem cells.

SUMMARY OF THE INVENTION

The present invention provides methods for production of mAbs specific for certain Pgp mutants and for Pgp in a biochemical conformation adopted in the presence of Pgp-mediated transport substrates or ATP depleting agents. The invention also provides methods for improving the sensitivity of and developing mAbs specific for Pgp in said biochemical conformation, and thereby provides improved cancer diagnostic and therapeutic methods and methods for developing anticancer drugs, and improved methods for blood stem cell purification. These methods are all based on the discovery by the present inventors that certain mAbs, particularly UIC2, are specific for Pgp in a biochemical conformation adopted in certain mutant embodiments of Pgp and in the presence of Pgp-mediated transport substrates and ATP depleting agents. The methods of the invention are based on enhanced antibody binding to Pgp in the presence of Pgp-mediated transport substrates or ATP depleting agents.

In a first aspect, the invention provides a method for producing an immunological reagent specific for P-glycoprotein in a biochemical conformation adopted by certain Pgp mutants and by Pgp in the presence of Pgp-mediated transport substrates or ATP depleting agents. In this aspect, the method comprises the steps of introducing a cell expressing a heterologous P-glycoprotein into an animal syngeneic with the species from which the cell was derived, wherein the heterologous Pgp molecule is in said biochemical conformation. The invention thus provides a method for producing immune cells in the animal expressing an antibody specific for this biochemical conformation of P-glycoprotein. In a preferred embodiment, the method of the invention provides a polyclonal antisera specific for P-glycoprotein in said biochemical conformation. In more preferred embodiments, the invention provides a monoclonal antisera specific for P-glycoprotein in said biochemical conformation. In the most preferred embodiment, the invention provides a hybridoma cell line that produces a monoclonal antibody specific for P-glycoprotein in said biochemical conformation. The invention also provides a monoclonal antibody produced using the methods of the invention.

In this aspect of the invention, a preferred embodiment of the P-glycoprotein in this specific biochemical conformation is achieved by providing a heterologous Pgp protein wherein particular amino acid residues in the ATP binding site of each half of the Pgp molecule are altered to provide a mutant or variant Pgp molecule. In preferred embodiments, the heterologous P-glycoprotein expressing-syngeneic cells express a mutant P-glycoprotein wherein each of the ATPase-specific active sites carry mutations that prevent ATP binding and/or ATP hydrolysis by these mutant Pgp proteins. In preferred embodiments, such mutants are characterized by amino acid substitution mutations in active site amino acid residues. In certain preferred embodiments, the substituted amino acid residues are lysine residues in the ATPase sites. In particularly preferred embodiments, the mutant the Pgp protein is human Pgp wherein the lysine residues at positions 433 and 1076 of the 1280 Pgp amino acid sequence are substituted with another amino acid, preferably methionine. In other preferred embodiments, the heterologous P-glycoprotein expressing-syngeneic cells express a mutant P-glycoprotein having amino acid substitution mutations at ATPase active site residues are glycine residues. In particularly preferred embodiments, the mutant the Pgp protein is human Pgp having glycine residues at positions 432 and 1075 of the 1280 Pgp amino acid sequence, preferably with serine residues.

In a second aspect, the invention provides a method for detecting functional P-glycoprotein expression in a mammalian cell, particularly a malignant mammalian cell and most particularly a multidrug resistant malignant mammalian cell. In this aspect of the invention the method comprises the steps of: (a) treating the mammalian cell with a P-glycoprotein substrate selected from the group consisting of reserpine, gramicidin, cyclosporine, vincristine, actinomycin D, taxol, verapamil and vinblastine or with an ATP-depleting agent; and then (b) reacting the mammalian cell with a detectably-labeled immunological reagent specific for P-glycoprotein in a biochemical conformation adopted in the presence of Pgp-mediated transport substrates or ATP depleting agents; and (c) detecting specific binding of the immunological reagent to the mammalian cell in the presence of the Pgp substrate or ATP depleting agent. In a preferred embodiment, the immunological reagent is a monoclonal antibody specific for P-glycoprotein in said biochemical conformation. In preferred embodiments, the immunological reagent is specific for a mutant form of Pgp wherein each of the lysine residues in the ATPase-specific active site of each half of the Pgp molecule has been changed to a residue other than lysine and preferably methionine. In a most preferred embodiment, the immunological reagent is the UIC2 monoclonal antibody (A.T.C.C. Accession No. HB 11027). Preferably, specific binding of the immunological reagent is increased in the presence of the Pgp substrate or ATP-depleting agent.

In a third aspect, the invention provides improved methods for functional P-glycoprotein specific staining using methods well-known in the art, including fluorescence-activated cell sorting, immunohistochemistry and similar staining methods. The invention also provides methods for discriminating between Pgp-specific and non-specific cell staining, whereby specific staining is associated with enhanced mAb staining of Pgp-expressing cells in the presence of a Pgp substrate or ATP depleting agent. In this aspect of the invention are provided methods wherein P-glycoprotein staining is achieved in the presence of a Pgp-mediated transport substrate or ATP-depleting agent, using an immunological reagent of the invention specific for Pgp in a biochemical conformation adopted in the presence of Pgp-mediated transport substrates or ATP depleting agents. In a preferred embodiment, the immunological reagent is a monoclonal antibody specific for P-glycoprotein in said biochemical conformation. In preferred embodiments, the immunological reagent is specific for a mutant form of Pgp wherein each of the lysine residues in the ATPase-specific active site of each half of the Pgp molecule has been changed to a residue other than lysine and preferably methionine. In a most preferred embodiment, the immunological reagent is the UIC2 monoclonal antibody (A.T.C.C. Accession No. HB 11027).

In a fourth aspect, the invention provides a method for identifying an immunological reagent, comprising antisera, antibodies, preferably monoclonal antibodies, and proteolytic or other Pgp-binding fragments thereof that are specific for P-glycoprotein in a biochemical conformation adopted by certain mutant embodiments of Pgp, and by Pgp in the presence of Pgp-mediated transport substrates or ATP depleting agents. This aspect of the methods of the invention is comprised of the steps: (a) reacting a mammalian cell expressing Pgp with a monoclonal antibody to be tested in the presence and absence of a P-glycoprotein substrate or ATP-depleting agent; and (b) detecting an increase in binding of a monoclonal antibody specific for P-glycoprotein in said biochemical conformation in the presence of a P-glycoprotein substrate or ATP-depleting agent. Preferably, the P-glycoprotein substrate is selected from the group consisting of reserpine, gramicidin, cyclosporine, vincristine, actinomycin D, taxol, verapamil and vinblastine.

In a fifth aspect, the invention provides a method for detecting and purifying lymphocytes and hematopoietic stem cells from a mammal, wherein the method comprising the steps of: (a) treating a biological sample comprising lymphocytes or hematopoietic stem cells with a P-glycoprotein substrate or ATP-depleting agent; (b) reacting the biological sample with a detectably-labeled immunological reagent specific for P-glycoprotein in a biochemical conformation adopted in the presence of Pgp-mediated transport substrates or ATP depleting agents; and (c) separating the lymphocytes or hematopoietic stem cells reacted with the detectably-labeled immunological reagent from the biological sample. In a preferred embodiment, the P-glycoprotein substrate is selected from the group consisting of non-toxic Pgp substrate, preferably cyclosporine and non-toxic derivatives thereof, and verapamil. In a preferred embodiment, the biological sample comprises blood, cord blood, lymph or bone marrow, with or without prior drug treatment. In a preferred embodiment, the immunological reagent is labeled with a detectable label, such as a fluorescent label, and the lymphocytes or hematopoietic stem cells reacted with the fluorescently-labeled immunological reagent. In preferred embodiments, lymphocytes or hematopoietic stem cells reacted with the detectably-labeled immunological reagent are separated from the biological sample by fluorescence-activated cell sorting, cell panning, immunomagnetic particles and other cell-separating means known in the art.

In a sixth aspect, the invention provides a method for improving detection of low levels of Pgp expression in mammalian cells, most preferably malignant mammalian cells and cells expressing the MDR phenotype, using the immunological detection methods of the invention. In preferred embodiments, the immunological detection methods include, but are not limited to, fluorescence activated cell sorting (FACS), most preferably providing an improvement of the sensitivity of FACS detection and isolation of cells expressing P-glycoprotein. In this aspect, the method comprises treating a population of mammalian cells comprising a mammalian cell expressing P-glycoprotein with a P-glycoprotein substrate or ATP depleting agent; reacting the population of mammalian cells with a fluorescently-labeled immunological reagent specific for P-glycoprotein in a biochemical conformation adopted in the presence of Pgp-mediated transport substrates or ATP depleting agents; and performing an immunological detection method such as fluorescence activated cell sorting on the mammalian cells. In a preferred embodiment, the P-glycoprotein substrate is selected from the group consisting of reserpine, gramicidin, cyclosporine, vincristine, actinomycin D, taxol, verapamil and vinblastine. In a preferred embodiment, the immunological reagent is a monoclonal antibody specific for P-glycoprotein in said biochemical conformation. In preferred embodiments, the immunological reagent is specific for a mutant form of Pgp wherein each of the lysine residues in the ATPase-specific active site of each half of the Pgp molecule has been changed to a residue other than lysine and preferably methionine. In a most preferred embodiment, the immunological reagent is the UIC2 monoclonal antibody (A.T.C.C. Accession No. HB 11027).

In a seventh aspect, the invention provides methods for identifying and selectively eliminating tumor cells expressing functional Pgp. In this aspect of the invention, the method comprises treatment of a mammalian cell, preferably a tumor cell, expressing functional P-glycoprotein with an immunological reagent, preferably a monoclonal antibody specific for Pgp in a biochemical conformation adopted in the presence of a Pgp substrate or ATP depleting agent, said treatment also being in the presence of a Pgp substrate or ATP depleting agent, whereby the immunological reagent further comprises a cytotoxic agent. In a preferred embodiment, the immunological reagent is a monoclonal antibody specific for P-glycoprotein in said biochemical conformation. In preferred embodiments, the immunological reagent is specific for a mutant form of Pgp wherein each of the lysine residues in the ATPase-specific active site of each half of the Pgp molecule has been changed to a residue other than lysine and preferably methionine. In a most preferred embodiment, the immunological reagent is the UIC2 monoclonal antibody (A.T.C.C. Accession No. HB 11027).

Also provided by the invention are methods for determining the antigenic epitope(s) of P-glycoprotein involved in mAb UIC2 binding and methods for producing antibodies specific for such epitopes.

The invention also provides methods for discriminating between multidrug resistance in mammalian cells resulting from the expression of functional Pgp and multidrug resistance related to the expression of the multidrug resistance related protein (the MRP gene product). In this aspect, the method comprises a showing of enhanced mAb binding in the presence of a Pgp substrate or ATP depleting agent as being specific for Pgp-mediated multidrug resistance.

Use of the methods of the invention for medical diagnostics of primary and malignant disease for detecting expression, particularly low-level expression, of P-glycoprotein is also provided by the invention.

The invention also provides a means for evaluating novel cytotoxic, chemotherapeutic drugs and Pgp inhibitors. The existing methods for screening and testing of new drugs that are Pgp inhibitors are based on the cytotoxicity or dye exclusion assays. These methods are costly, laborious and time-consuming. A screening test based on the enhanced binding of UIC2 mAb or its derivatives in the presence of Pgp substrates enables the rapid, reliable and cost-effective characterization of potential new Pgp-targeted drugs.

Specific preferred embodiments of the present invention will become evident from the following more detailed description of certain preferred embodiments and the claims.

DESCRIPTION OF THE DRAWINGS

FIGS. 1A through 1H depicts the predicted nucleic acid sequence of human Pgp (Seq. I. D. No. 1), wherein the initiation (ATG) and termination (TGA) codons, as well as codons encoding mutations at amino acid positions 433 and 1076, are underlined.

FIGS. 6A through 6D illustrates flow cytometric analysis of mouse L cell transfectants expressing wildtype (KK-L; FIGS. 6A and 6B), or double mutant (MM; FIGS. 6C and 6D) human Pgp incubated with PE-conjugated UIC2 (FIGS. 6A and 6C) or MRK16 (FIGS. 6B and 6D) in the presence of absence of taxol, vinblastine or etoposide.

FIGS. 7A through 7F illustrate flow cytometric analysis of mouse L cell transfectants expressing wildtype (KK-H) or single mutant (KM-H and MK-H) human Pgp incubated with PE-UIC2 (FIGS. 7A, 7C and 7E) or PE-MRK16 (FIGS. 7B, 7D and 7F) in the presence or absence of vinblastine, taxol or etoposide.

FIG. 8A or KK-H; FIG. 8B), single mutant (MK-H; FIG. 8C; or KM; FIG. 8D) or double mutant (MM; FIG. 8E) human Pgp incubated with PE-conjugated UIC2 in the presence or absence of vinblastine and the ATP depletion agents oligomycin, azide and cyanide.

DETAILED DESCRIPTION OF THE PREFERRED EMBODIMENTS

Figure 2A:
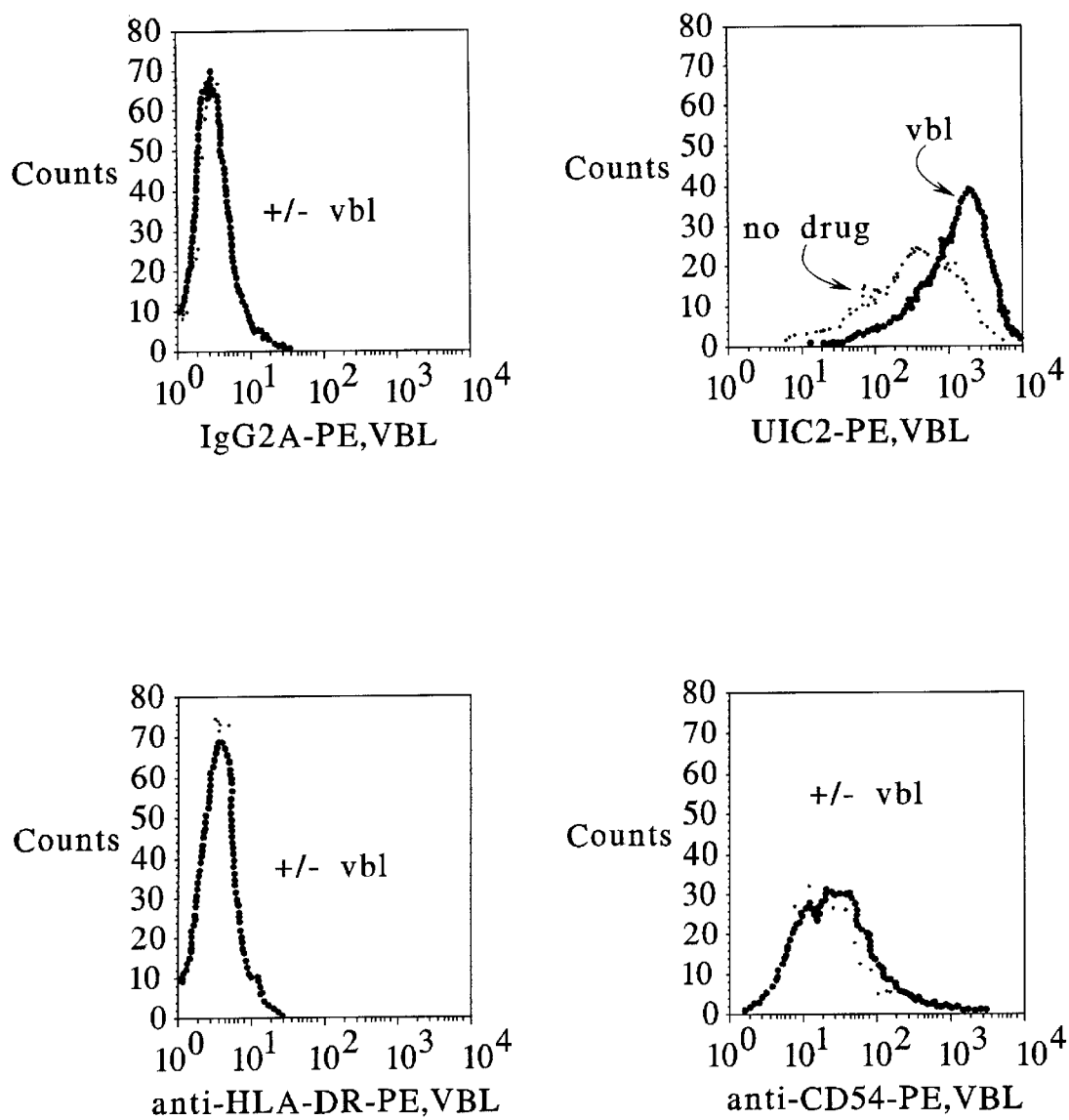
FIG. 2A illustrates flow cytometric analysis of K562/I-S9 leukemia cells incubated with phycoerythrin (PE)-conjugated mAb in the presence or absence of vinblastine.

The present invention provides a variety of methods related to P-glycoprotein mediated multidrug resistance in mammalian, most preferably human, cells. For the purposes of the present invention, "multidrug resistance" is defined as cross-resistance to at least the following cytotoxic drugs: vinblastine, vincristine, doxorubicin, colchicine, actinomycin D, etoposide, taxol, puromycin, and gramicidin D; it will be recognized that cross-resistance to other cytotoxic drugs also falls within the meaning of multidrug resistance as it is understood by those with skill in the art. Such drugs are generally referred to herein as MDR drugs.

The methods of the invention are based in significant part on the discovery by the present inventors that the mAb UIC2, which is capable of inhibiting drug efflux from Pgp-expressing cells, specifically binds to Pgp in a particular biochemical conformation. For the purposes of this invention this biochemical conformation is functionally defined as the conformation adopted by human Pgp in the presence of Pgp substrates or ATP depleting agents, and results in enhanced binding of the mAb UIC2. Also within this definition are certain mutant forms of Pgp having disabling mutations in the nucleotide binding sites, wherein ATPase activity us disabled, as described below, in Loo and Clarke (1995, J. Biol. Chem. 270: 21449–21452) and in Müller et al. (1996, J. Biol. Chem 271: 1877–1883). For the purposes of this invention, exemplary Pgp transport substrates include a variety of lipophilic, cytotoxic natural product drugs used in cancer chemotherapy, including but not limited to Vinca alkaloids, epipodophyllotoxins, anthracyclines, etoposide, colchicine, colcemid and taxol, as well as the antibiotics monensin and actinomycin D and the interleukin cytokines. For the purposes of this invention, the term "ATP-depleting agent" is intended to include, but is not limited to, 2-deoxyglucose, cyanine, oligomycin, valinomycin and azide, as well as salts and derivatives thereof.

The invention provides methods for detecting functional P-glycoprotein expression in a mammalian cell, particularly a malignant mammalian cell and most particularly a multidrug resistant malignant mammalian cell. For the purposes of this invention, the term "functional Pgp expression" is intended to encompass the production of Pgp protein in a cell membrane, most preferably the plasma membrane, wherein the Pgp is capable of transporting an MDR drug across said membrane and against a concentration or solubility gradient. "Functional Pgp expression" is also intended to encompass Pgp protein molecules having an ATPase activity.

In the methods of the invention provided to detect functional Pgp expression in a mammalian cell, the immunological reagent is preferably provided wherein the extent and amount of specific binding of the reagent to Pgp expressed by the mammalian cell is increased in the presence of a Pgp substrate or ATP-depleting agent. For the purposes of this invention, it will be understood that the invention thus provides methods and reagents wherein specific binding of the immunological reagents is enhanced in the presence of a Pgp substrate or ATP-depleting agent, as compared with specific binding of the immunological reagent to the mammalian cell in the absence of a Pgp substrate or ATP-depleting agent. Such enhanced binding is detected using any method known to the skilled artisan, including but not limited to detection of binding of detectably-labeled embodiments of the immunological reagents of the invention, and detection of specific binding of the immunological reagents of the invention using a detectably-labeled immunological reagent that is specific for the immunological reagents of the invention (e.g., in a "sandwich-type" immunoassay).

In particular, the invention provides methods and immunological reagents for purifying hematopoietic stem cells from a biological sample, such as bone marrow or human cord blood. As provided by the invention such methods include conventional cell separation methods and techniques, including but not limited to fluorescence activated cell sorting techniques, and more specifically to the use of immunomagnetic beads and immunoaffinity columns for achieving cell separation. It will be recognized that in the practice of the methods of the invention using these separation techniques, the immunological reagents of the invention are provided in certain embodiments conjugated to immunomagnetic beads or immunoaffinity columns, to achieve separation of hematopoietic stem cells based on expression of Pgp. In other embodiments, the methods of the invention are provided wherein the immunological reagents of the invention are recognized by immunomagnetic bead-conjugated or immunoaffinity column-conjugated second immunological reagents which specifically recognize the immunological reagents of the invention (for example, based on isotypic, allotypic or species-specific antibodies or antisera). Also encompassed within the immunological detection methods useful in the practice of the invention are immunological reagents labeled with a fluorescent label and separation of the hematopoietic cells reacted with the fluorescently-labeled immunological reagent from other cells in the biological sample by fluorescence activated cell sorting. Alternative separation methods depending on specific and enhanced recognition of Pgp using the immunological reagents of this invention will be understood by those with skill in the art and are encompassed within the methods of the invention.

The invention provides methods for improving detection of low levels of Pgp expression in mammalian cells, most preferably malignant mammalian cells and cells expressing the MDR phenotype, using immunological detection methods. For the purposes of this invention, the term "low levels of Pgp expression" is intended to encompass expression levels at the lower limit of detection using conventional immunological and other techniques. Those having ordinary skill in the art will understand this description of "low level" expression as it has been disclosed, for example, for the human epithelial carcinoma cell lines KB-3–1 and KB-8 by Noonan et al. (1990, *Proc. Natl. Acad. Sci. USA* 87: 7160–7164; Gottesman et al., 1991, in *Molecular and Cellular Biology of Multidrug Resistance in Tumor Cells*, Plenum Press, N.Y.).

The invention also provides methods and immunological reagents useful in detecting Pgp expression and using such expression for hematopoietic cell purification, cancer diagnostics and therapeutics, and methods for producing Pgp-specific immunological reagents. For the purposes of this invention, the term "immunological reagents" is intended to encompass antisera and antibodies, particularly monoclonal antibodies, as well as fragments thereof (including F(ab), F(ab)$_2$, F(ab)' and F, fragments). Also included in the definition of immunological reagent are chimeric antibodies, humanized antibodies, and recombinantly-produced antibodies and fragments thereof. Immunological methods used in conjunction with the reagents of the invention include direct and indirect (for example, sandwich-type) labeling techniques, immunoaffinity columns, immunomagnetic beads, fluorescence activated cell sorting (FACS), enzyme-linked immunosorbent assays (ELISA), and radioimmune assay (RIA). For use in these assays, the Pgp-specific immunological reagents can be labeled, using fluorescence, antigenic, radioisotopic or biotin labels, among others, or a labeled secondary immunological detection reagent can be used to detect binding of the Pgp-specific immunological reagents (i.e., in secondary antibody (sandwich) assays).

The UIC2 mAb is one example of the immunological reagents of the invention. This mAb is directed to an epitope in an extracellular domain of human Pgp, and was made by immunizing mice with mouse cells that have been made MDR by transfection with an isolated human MDR1-encoding cDNA (see U.S. patent application Ser. No. 07/626,836, incorporated by reference). Briefly, immunogenic cells (preferably transfected syngeneic mouse fibroblasts) were used to immunize BALB/c mice (e.g., transfected BALB/c mouse 3T3 fibroblasts). MDR derivatives of mouse BALB/c 3T3 fibroblasts were generated with human MDR1-encoding DNA, and cells selected and grown in cytotoxic concentrations of an MDR drug. Once produced, MDR fibroblasts were selected in which the transfected MDR1 gene had been amplified, by consecutive steps of selection in progressively higher concentrations of an MDR drug. This produced highly multidrug resistant cells that expressed large amounts of Pgp inserted into the cellular plasma membrane resulting in high levels of MDR (e.g., BALB/c 3T3-1000 cells are resistant to vinblastine at a concentration of 1000 ng/mL).

Such cells were used to immunize syngeneic mice. Appropriate numbers of cells were injected subcutaneously (s.c.) or intraperitoneally (i.p.) by art-recognized immunization protocols (see co-owned and co-pending U.S. patent application Serial No. 07/854,881, filed Mar. 20, 1992, now U.S. Pat. No. 5,434,075, issued Jul. 18, 1995, and Ser. No. 08/032,056, filed Mar. 16, 1993, each of which is incorporated in their entirety herein). Typically, $10^5$ to $10^8$ transfected cells were injected 5 or 6 times at two week intervals, and a final boosting was done with, for example, $10^6$ cells subcutaneously and/or intravenously. At an appropriate time after the booster injection, typically 3 to 5 days thereafter, the spleen was harvested from a hyperimmune mouse, and hybridomas generated by standard procedures (see, e.g., Kearney et al., 1979, *J. Immunol.* 123: 1548) using human myeloma cells, for example, P3-X63-Ag 8.653 (A.T.C.C., Rockville, Md.).

Extracellular fluids from individual hybridoma cultures were screened for specific mAb production by conventional methods, such as by indirect immunofluorescence using non-Pgp expressing control cells (e.g. non-transfected fibroblasts) and human Pgp-expressing (e.g. BALB/c 3T3-1000) cells affixed to glass slides, and FITC-labeled goat anti-mouse polyvalent immunoglobulins (Sigma Chemical Co., St. Louis, Mo.) as the secondary, reporter antibody. The particular screening method used was not critical provided that it was capable of detecting anti-human MDR1 Pgp mAb. It is important, however, that cells are not permeabilized and fixed during screening (i.e., they are living cells), so that only antibodies reactive with extracellular protein domains are detected.

A stable hybridoma producing the UIC2 mAb was established by conventional methods, such as by consecutive rounds of subcloning by, e.g., end-point dilution, and screening the culture medium for monoclonal antibodies. The hybridoma was propagated by, for example, growth in ascites fluid in vivo in syngeneic animals, and the secreted antibody isolated and purified from ascites fluid by affinity chromatography with a Sepharose-Protein A matrix specific for an IgG isotype. It will be understood that other procedures for immunoglobulin purification well known in the art are also useful for producing hybridomas that express Pgp-specific antibodies.

Alternative methods for producing mAbs are known in the art (as described in co-owned and co-pending U.S. patent application Ser. No. 07/854,881, filed Mar. 20, 1992, now U.S. Pat. No. 5,434,075, issued Jul. 18, 1995, and Ser. No. 08/032,056, filed Mar. 16, 1993, each of which is incorporated in its entirety herein).

mAbs produced by the UIC2 hybridoma, as well as fragments and recombinant derivatives thereof, were characterized as to immunoglobulin isotype, reactivity with different Pgp-expressing cell lines and binding to Pgp in MDR cells using art-recognized techniques (see U.S. Pat. No. 5,434,075, issued Jul. 18, 1995, incorporated by reference). As provided herein, preferred mAbs of the invention specifically bind to Pgp in a biochemical conformation adopted in the presence of Pgp-mediated transport substrates or ATP depleting agents, or in certain Pgp mutants as described herein.

The present invention provides for improved production of mAbs specific for Pgp in a biochemical conformation adopted by certain mutant embodiments of Pgp, and in the presence of Pgp-mediated transport substrates or ATP depleting agents. Specifically, the invention provides certain Pgp mutants that adopt such a conformation without regard to the presence or absence of Pgp-mediated transport substrates or ATP depleting agents. Means and methods of mAb production described herein are useful in this regard, the specificity of the mAb arising from the conformation of the Pgp antigen(s) used as immunogen(s).

The immunological reagents of the invention provided specifically recognize and bind to Pgp, preferably human Pgp, in a conformation adopted in the presence of Pgp substrates, ATP depleting agents, and certain mutant embodiments of Pgp. As used herein, the term "mutant embodiments of Pgp" is intended to encompass heterologous Pgp protein wherein particular amino acid residues in the ATP binding site of each half of the Pgp molecules are altered to provide a mutant or variant Pgp molecule. In preferred embodiments, the heterologous P-glycoprotein expressing-syngeneic cells express a mutant P-glycoprotein wherein each of the ATPase-specific active sites carry mutations that prevent ATP binding and/or ATP hydrolysis by these mutant Pgp proteins. In preferred embodiments, such mutants are characterized by amino acid substitution mutations in active site amino acid residues. In certain preferred embodiments, the substituted amino acid residues are lysine residues in the ATPase sites. In other preferred embodiments, the substituted amino acid residues are glycine residues. In particularly preferred embodiments, the mutant Pgp protein in human Pgp wherein the lysine residues at positions 433 and 1076 of the 1280 Pgp amino acid sequence are substituted with another amino acid, preferably methionine. In other preferred embodiments, the heterologous P-glycoprotein expressing-syngeneic cells express a mutant P-glycoprotein having amino acid substitution mutations at ATPase active site glycine residues, preferably glycine residues at positions 432 and 1075 of the 1280 Pgp amino acid sequence. Preferably, said glycine residues are substituted with serine residues. It will be understood by those with skill in the art that substitutions within the ATP binding sites may involve other amino acid residues or comprise substitutions with other amino acids than the preferred methionine or serine residues explicitly mentioned here. All such ATPase active site mutants of Pgp are intended to fall within the scope of this disclosure.

The effect of anti-Pgp mAbs, fragments or recombinant derivatives thereof on Pgp function was assessed by studying the efflux of fluorescent or radioactively labeled drugs from NMR cells in the presence of absence of mAb. The effects of antibody preparations on drug cytotoxicity were assessed by incubating suspensions of MDR and control cells with the antibody preparation, then testing for cell growth inhibition in the absence and presence of an anticancer drug such as one of the Vinca alkaloids. Such assays are by definition preferred, as the mAbs of the invention are intentionally provided to be specific for substrate-bound Pgp.

Fragments of the UIC2 mAb that maintain the antigenic specificity of the complete antibody are derived by enzymatic, chemical or genetic engineering techniques (for example, partial digestion with proteolytic enzymes such as papain, pepsin or trypsin; papain digestion produces two Fab fragments and one $F_c$ fragment, while pepsin cleavage releases $F(ab)_2$ (two antigen-binding domains bound together) fragments). mAb fragments lacking the constant ($F_c$) portion are advantageous over the complete antibody for in vivo applications, as such fragments are likely to possess improved tissue permeability. Furthermore, many cells and tissues in the body express receptors capable of binding to the $F_c$ portion of antibodies, resulting in undesirable nonspecific binding of the complete antibody.

The methods of the invention are not intended to be limited in scope to immunological reagents comprising the UIC2 mAb and hybridomas producing this mAb. The invention provides a variety of methods, all related to specific binding of mAbs to Pgp in a biochemical conformation adopted in the presence of Pgp-mediated transport substrates or ATP depleting agents. The UIC2 mAb is provided solely as one illustrative example of an mAb that specifically binds to Pgp and mutants thereof having such a biochemical conformation.

The Examples which follow are illustrative of specific embodiments of the invention, and various uses thereof. They set forth for explanatory purposes only, and are not to be taken as limiting the invention.

EXAMPLE 1

1. Cell lines. Monoclonal antibodies. and Reagents

MRK-16 mAb ($IgG_{2a}$) was obtained from Dr. T. Tsuruo, University of Tokyo, Japan. UIC2 was produced from UIC2 and UIC2/A hybridomas as described in U.S. Pat. No. 5,434,075, issued Jul. 18, 1995.

All mAb samples were at least 95% pure according to SDS-PAGE. Concentrations of the mAb were determined by the quantitative mouse Ig radial immunodiffusion kit (ICN, Costa Mesa, Calif.). When necessary, mAb's were further concentrated and dialyzed against phosphate-buffered saline (PBS) or Dulbecco modified Eagle's medium (DMEM). mAbs were conjugated with R-phycoerythrin (PE) or fluorescein isothiocyanate (FITC) at 1:1 (PE) and 1:4 (FITC) mAb:label and purified using standard techniques (Maino et al., 1995, Cytometry 20: 127–133). $IgG_{2a}$-PE conjugates were purchased from Becton-Dickinson Immunocytometry Systems (BDIS, San Jose, Calif.) and used as a negative isotype control for nonspecific staining.

The K562/Inf cell line was derived by infection of human K562 leukemia cells with a recombinant retrovirus pLMDR1L6 carrying human MDR1 cDNA (Choi et al., 1991, Proc. Natl. Acad. Sci. USA 88: 7386–7390), and subsequently subcloned without cytotoxic selection (e.g., by FACS sorting based on Pgp-specific immunostaining or Pgp-mediated efflux of fluorescent dyes). Clones expressing relatively high levels of Pgp were selected by repeated selection of Pgp-positive clones by FACS after clonal expansion. Clone K562/I-S9 is one such FACS-selected clone (produced as described in Weisberg et al., 1996, J. Exp. Med. 183: 2699–2704).

LMtk cells transformed with wildtype and mutant forms of P-glycoprotein were prepared according to Morse (1996, Doctoral Dissertation, Department of Genetics, University of Illinois at Chicago, incorporated by reference herein). MDR1 cDNA-comprising constructs encoding wildtype (KK), single mutant (KM, MK) and double mutant (MM) forms of P-glycoprotein were prepared as described in Morse, wherein the mutant forms have a lysine→to—methionine mutation within either (single mutant) or both (double mutant) of the consensus ATP binding sites in the amino- and carboxyl-terminal halves of P-glycoprotein, introduced at amino acid positions 433 and 1076 by site-directed mutagenesis techniques (see Kramer et al., 1984, Nucleic Acids Res. 12: 9441–9456; Carter et al., 1985, Nucleic Acids Res. 13: 4431–4443). Each of these constructs further comprises the bacterial neomycin-resistance gene (neo), fused to the MDR1 gene via an overlapping translation termination/initiation codon (ATGA). As a consequence, MDR1 and neo are expressed in mammalian cells in a bicistronic messenger RNA. The MDR1-encoding portions of these constructs are shown in Seq. I.D. No. 1. These sequences, cloned into the mammalian expression vector expression vector pUCFVX were introduced into LMtk cells by calcium phosphate coprecipitation or electroporation (see Sambrook et al., ibid.) and transfectants selected in G418 (Grand Island Biological Co. (GIBCO), Long Island, N.Y.)-containing media. Clonal populations of Pgp wildtype or mutant-expressing cells expressing approximately equal amounts of Pgp at the cell surface were selected by FACS using fluorescently labeled mAb MRK16 and were then expanded under G418 selection.

All chemotherapeutic drugs were purchased from Sigma Chemical Co. (St. Louis, Mo.), diluted in water, DMSO or alcohol, aliquoted and stored at +4° C. for 10–14 days or at 20° C. until use.

2. Preparation of anti-Pgp Monoclonal Antibodies

Monoclonal antibodies specific for human P-glycoprotein were prepared as disclosed in co-owned and co-pending U.S. patent application Ser. No. 07/854,881, filed Mar. 20, 1992, now U.S. Pat. No. 5,434,075, issued Jul. 18, 1995, and Ser. No. 08/032,056, filed Mar. 16, 1993, each of which is incorporated in its entirety herein.

Briefly, mouse fibroblast BALB/c 3T3 cells expressing the MDR1 gene encoding P-glycoprotein (Pgp) were derived by transfecting fibroblasts with isolated human MDR1 cDNA in a eukaryotic expression vector pUCFVXMDR1 (Choi et al., 1988, Cell 5: 519–529), isolating multidrug-resistant cells after cytotoxic selection in 20 ng/mL of vinblastine, and subsequently amplifying the transfected gene by consecutive steps of selection in 250 ng/mL, 500 ng/mL and 1000 ng/mL of vinblastine. The resultant multidrug-resistant fibroblasts were termed BALB/c 3T3-250, BALB/c 3T3-500 and BALB/c 3T3-1000, respectively.

BALB/c mice were immunized with $1-2 \times 10^7$ of BALB/c 3T3-1000 cells, injected subcutaneously (s.c.) and/or intraperitoneally (i.p.) six times at two-week intervals. The final immunogenic boost was done with $2 \times 10^7$ cells i.p., and $5 \times 10^6$ cells administered intravenously (i.v.). Four days after the last administration of fibroblasts, the spleen from one animal was removed, and hybridomas generated by art-recognized techniques using the human myeloma cell line P3-X63-Ag8.653 (A.T.C.C. Accession No. CRL-1580).

Tissue culture supernatant fluids from individual hybridomas were screened for monoclonal antibody (mAb) production by indirect immunofluorescence labeling of live BALB/c 3T3 and BALB/c 3T3-1000 cells attached to glass slides. Fluorescein isothiocyanate (FITC)-labeled goat anti-mouse polyvalent immunoglobulins (obtained from Sigma Chemical Co., St. Louis, Mo.) were used as a secondary antibody reagent at 1:100 dilution. Of 556 tested hybridomas, mAb produced by only two hybridomas reacted with BALB/c 3T3-1000 cells, and of these two only one hybridoma (termed UIC2) produced an antibody reactive with BALB/c 3T3-1000 cells, but not with control BALB/c 3T3 cells.

A stable hybridoma line secreting UIC2 mAb was established by three consecutive rounds of subcloning by end-point dilution and screening of the supernatant fluids, as described in co-owned and co-pending U.S. patent application Ser. No. 07/854,881, filed Mar. 20, 1992, now U.S. Pat. No. 5,434,075, issued Jul. 18, 1995, and Ser. No. 08/032,056, filed Mar. 16, 1993, each of which is incorporated in its entirety herein.

The UIC2 hybridoma was propagated as ascites in syngeneic BALB/c mice, and the immunoglobulin was purified from ascites fluid by Sepharose-Protein A (Bio-Rad, Richmond, CA) affinity chromatography. UIC2 mAb, tested by SDS-PAGE, was at least 95% pure IgG. The UIC2 hybridoma is on deposit in the American Type Culture Collection, Rockville, Md. (U.S.A.) (Accession No. HB11027) and is available to the public.

Application of Ouchterlony and immunoblotting tests using a standard set of anti-mouse Ig antibodies revealed that the UIC2 mAb belongs to the $IgG_{2a}$ subclass.

UIC2 mAb was shown to induce complement-mediated cytotoxicity using Low-Tox-M rabbit complement (Cedarland Labs, Hornby, Ontario) on BALB/c, BALB/c 3T3-1000, CEM/$VLB_{100}$, K562 and K562/Inf cell lines.

3. Fluorescence Activated Cell Sorting/Flow Cytometry Analysis

Cells were trypsinized, when necessary, and washed twice with PBS at room temperature or 4° C. and distributed in 2 mL conical plastic tubes at a concentration of $10^6$ cells/tube in 1 mL of pre-warmed (37° C) $Ca^{++}$-, $Mg^{++}$-free PBS and incubated for 37° C. for 10 min. Thereafter, aliquots of 20 $\mu$L of drug stock solutions at 1 mg/mL (or at different concentrations, when necessary) were added. The cells were incubated with drugs at 37° C. for 10 min. Aliquots of 50 AL mAb stock solutions (UIC2 conjugated with R-phycoerythrin (UIC2-PE), MRK16-PE, and IgG2a-PE conjugates, or UIC2 conjugates with fluorescein isothiocyanate (UIC2-FITC) and IgG2a-FITC conjugates), prepared at 1:10 dilution, were added and the tubes mixed thoroughly. The amount of mAb added per $10^6$ cells/mL were determined by preliminary titration. mAb stock solutions were used at a concentration of 0.08 mg/mL in all experiments with chemotherapeutic drugs. After incubation with mAb for 20–30 minutes, cells were washed twice with ice-cold PBS, transferred into plastic tubes containing 0.5 mL ice-cold PBS and 1 $\mu$g/mL propidium iodide, and kept on ice until FACS analysis. For indirect staining experiments, cell samples were washed twice, stirred, incubated with secondary antibody reagents in 100 $\mu$L PBS for 20 min. and prepared as above for FACS analysis. For ATP depletion experiments, washed cells were incubated with 20 $\mu$L aliquots of stock solutions of azide, oligomycin or cyanide for 15 min. at 37° C. and then immediately treated with chemotherapeutic drugs, antibodies and propidium iodide as described above.

Cells were analyzed by FACSort (BDIS) equipped with an argon laser (Cyonics) tuned to 488nm, using 4 parameters: (forward scatter, side scatter, FL1 for FITC, FL2 for PE conjugates and FL3 for propidium iodide); dead cells were excluded on the basis of forward and side scatter and PI (FL3) staining. The FACS data were analyzed by the Lysis II or CellQuest computer programs.

4. ATP Depletion Experiments

Cells were depleted of intracellular ATP by incubation with oligomycin, azide or cyanide at various concentrations under conditions described in Section 3 above. Intracellular ATP was measured using the Bioluminescent Somatic Cell Assay kit (Sigma, St. Louis, MO), whereby the amount of ATP in cell lysates is proportional to light emitted by firefly luciferase. Intracellular ATP was expressed relative to the amount present in cells treated with PBS instead of ATP depleting agents. After incubation of cell lysates with the components of the assay kit, 0.1 mL of the reaction solution was assayed spectrophotometrically over a wavelength range of 390–622 nm using an AutoLumat LB953 Universal Luminometer (EG&G Berthold, Vildbad, Germany). All measurements were performed at 8° C. in 12×75 mm polystyrene cuvettes (Analytical Luminescence Lab, San Diego, Calif.).

EXAMPLE 2 mAb UIC2 Reactivity Is Increased in the Presence of Pgp-transported Compounds Flow cytometry was used to analyze the reactivity of phycoerythrin (PE)—conjugated mAbs UIC2 and MRK16 with Pgp-expressing cells in the presence of different drugs. The range of optimal drug concentrations for these experiments (1–5 mg/mL) was determined by a series of preliminary titration experiments.

Figure 2B:
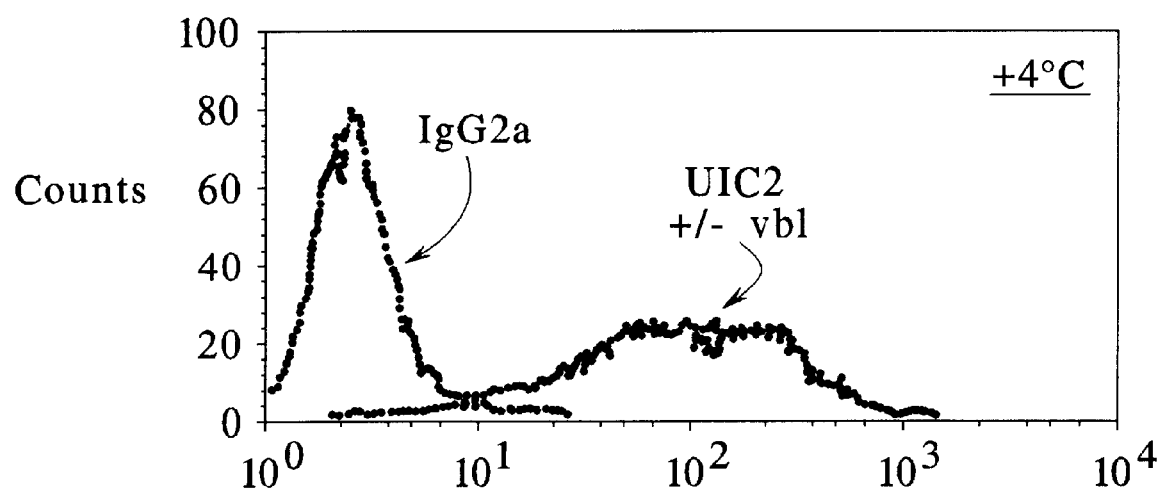
FIG. 2B illustrates flow cytometric analysis of K562/I-S9 leukemia cells incubated with PE-conjugated UIC2 mAb in the presence or absence of vinblastine at 4° C.
Figure 3A:
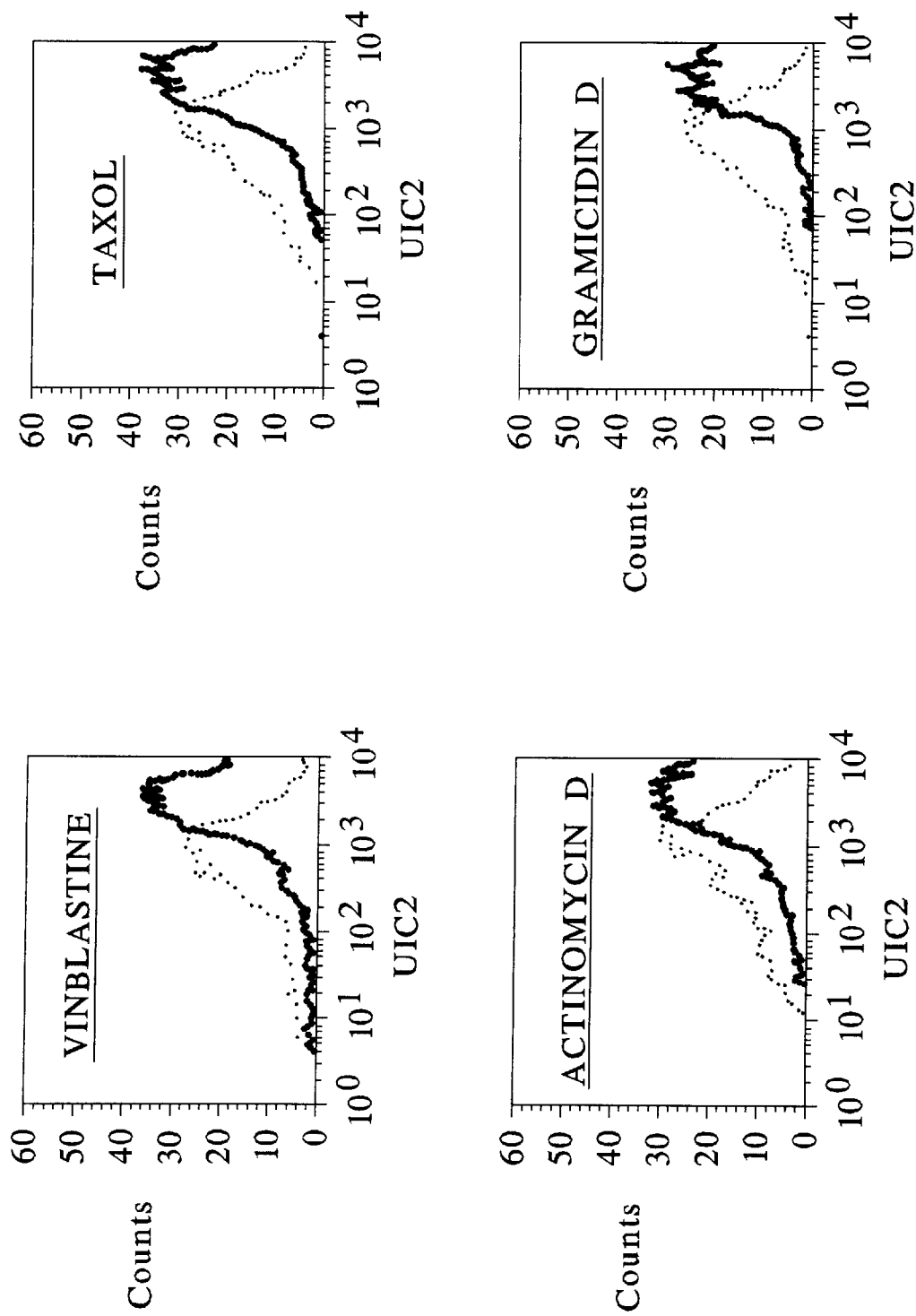
FIGS. 3A and 3B illustrate flow cytometric analysis of K562/i-S9 leukemia cells incubated with PE-conjugated UIC2 mAb (FIG. 3A) or MRK16 mAb (FIG. 3B) in the presence or absence of different cytotoxic drugs.
Figure 3A:
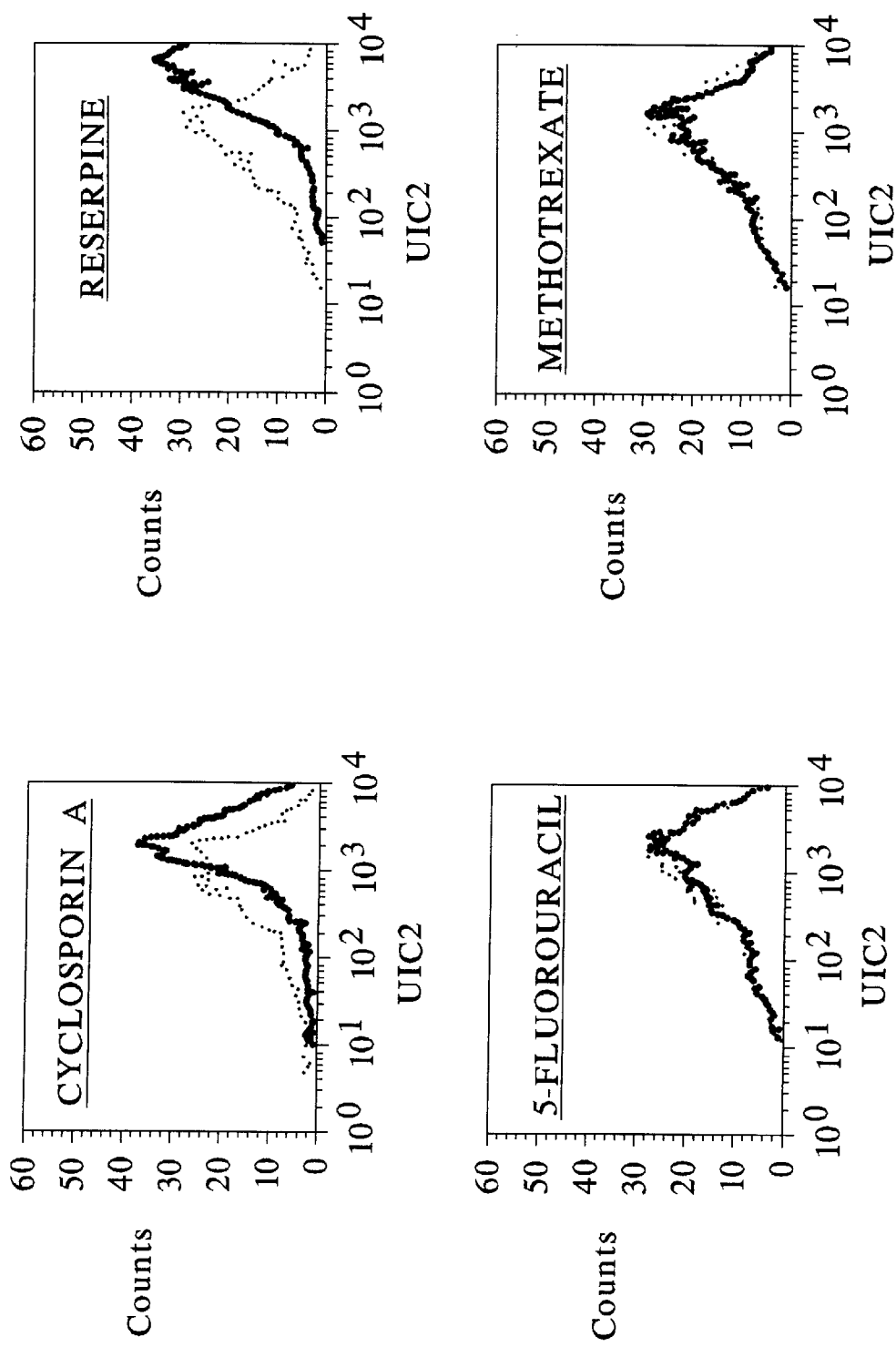
Figure 3B:
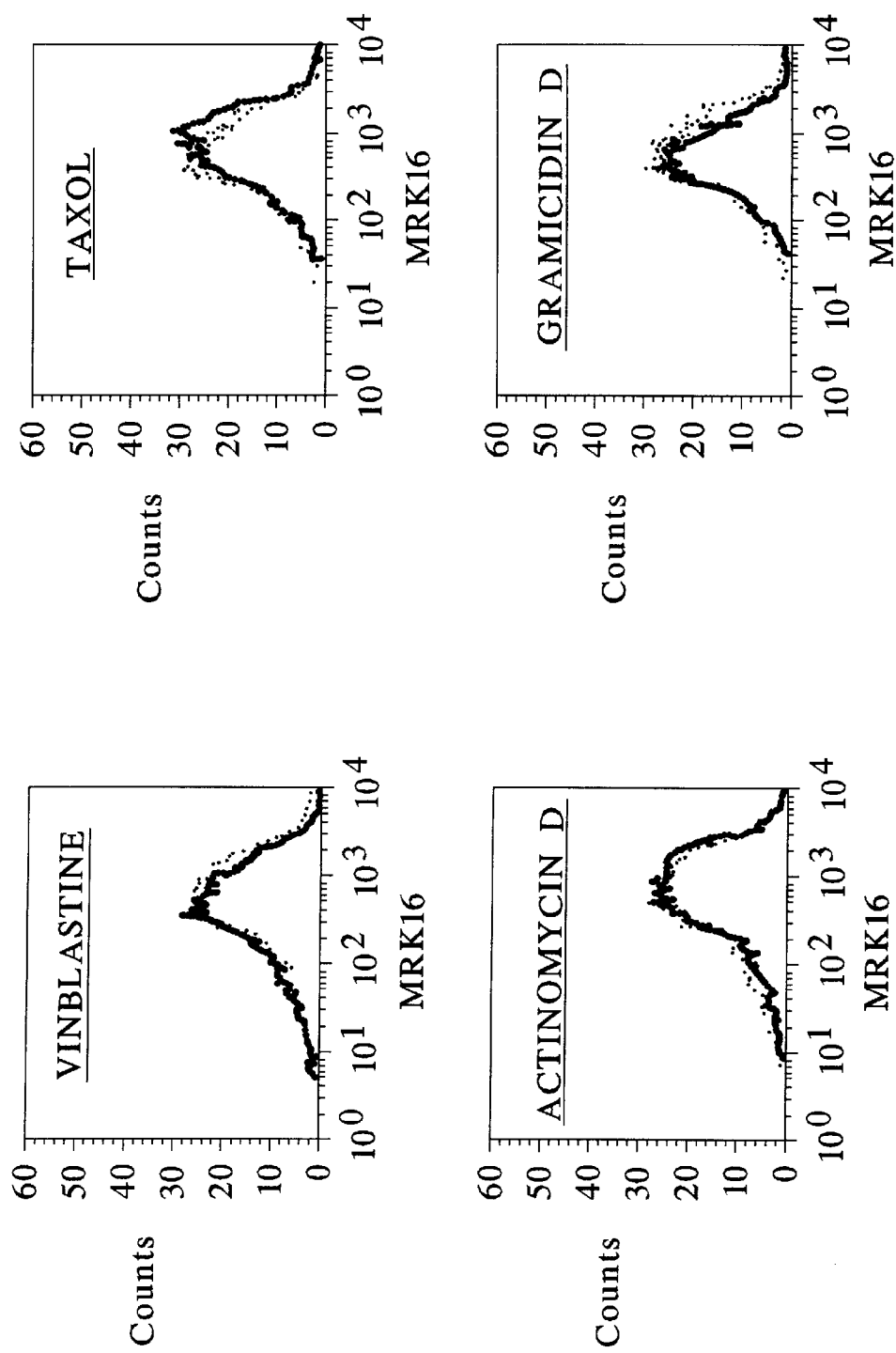
Figure 3B:
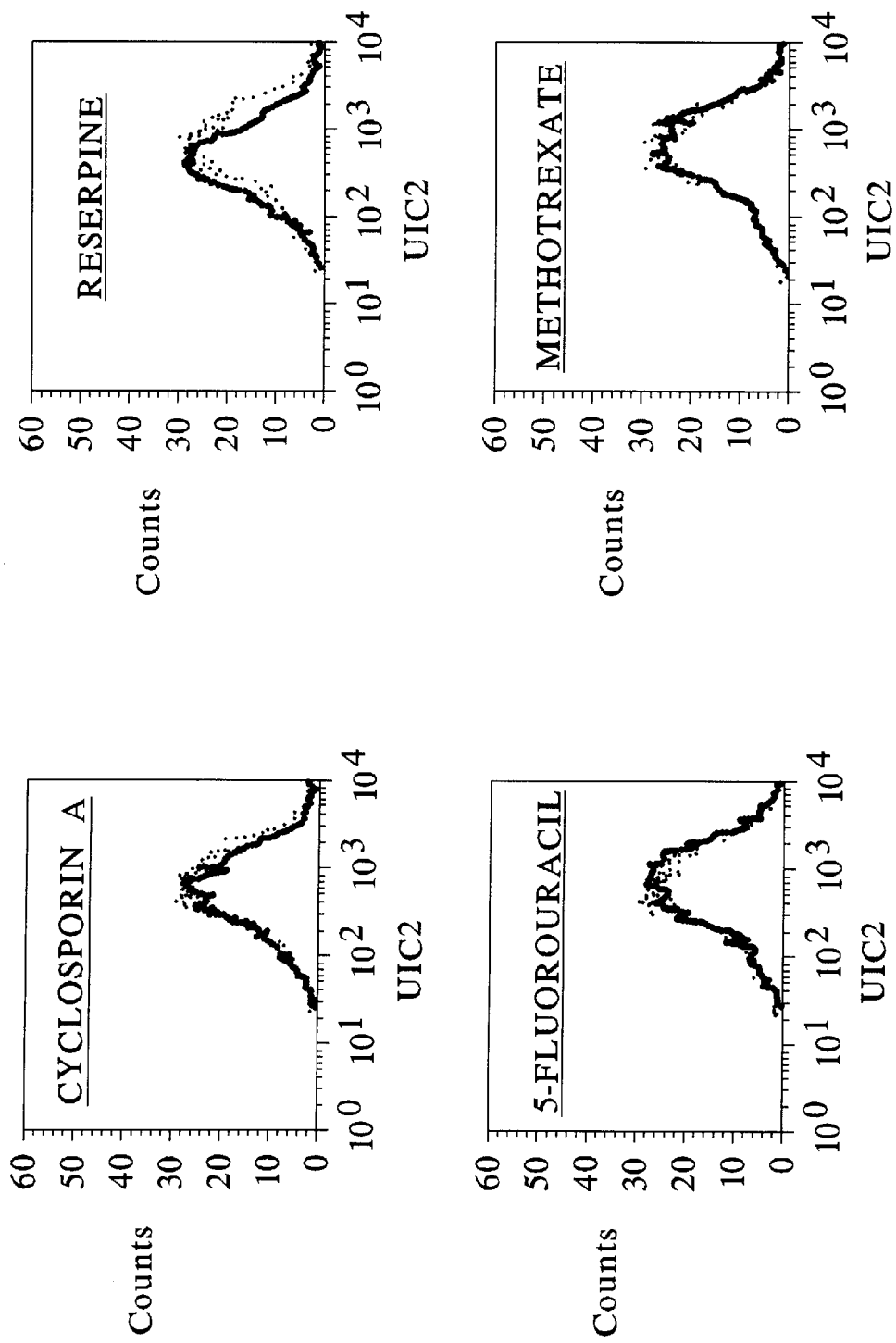
Figure 4:
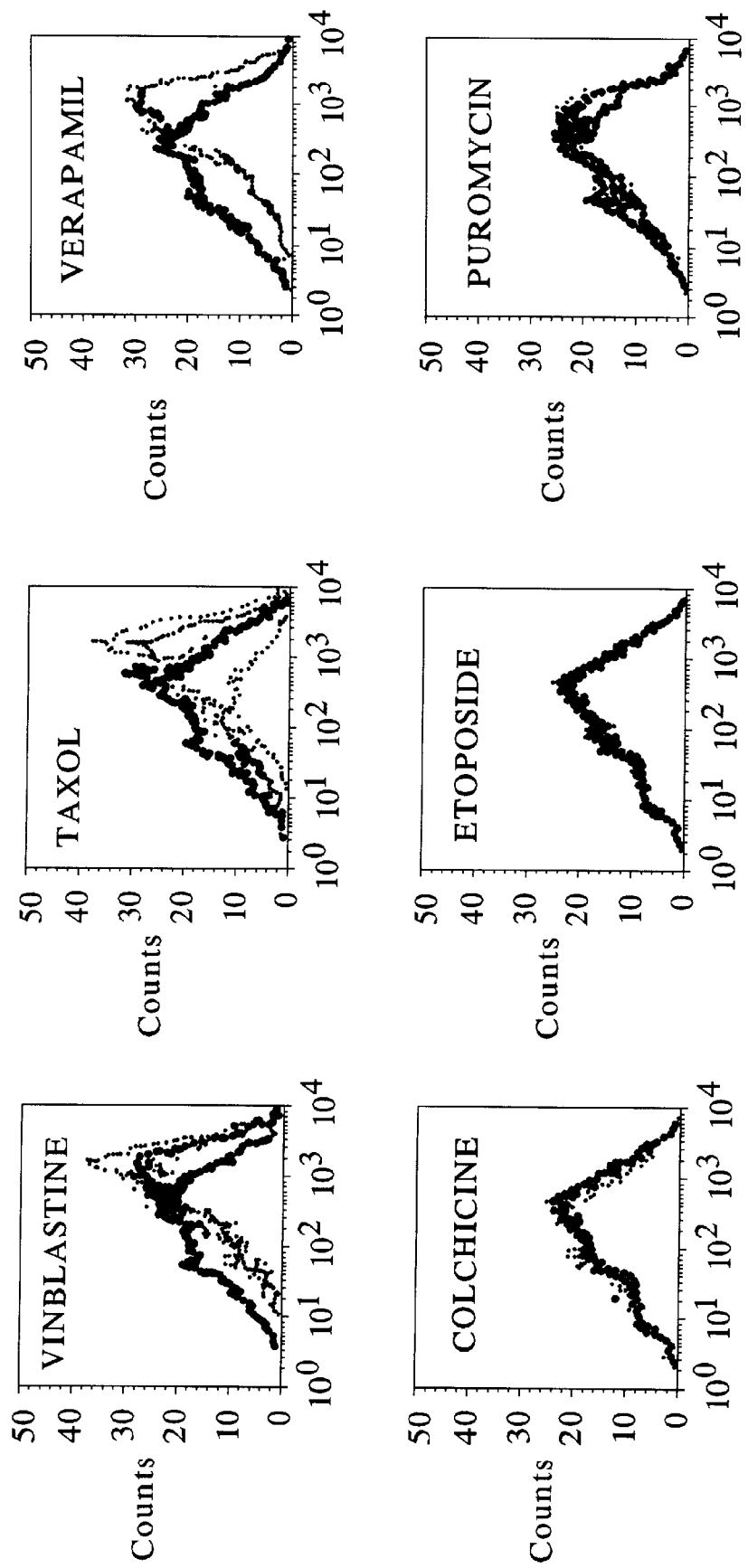
FIG. 4 illustrates flow cytometric analysis of K562/i-S9 leukemia cells incubated with PE-conjugated UIC2 mAb in the presence of increasing concentrations of vinblastine (1–625 $\mu$M), taxol (0.96–600 $\mu$M), verapamil (1.8–1125 $\mu$M), colchicine (2–1250 $\mu$M), etoposide (1.36–850 $\mu$M) and puromycin (1.72–1075 $\mu$M).

FIG. 2A illustrates the results obtained with K562/I-S9 leukemia cell line, which was selected to express Pgp by infecting K562 cells with a MDR I-transducing recombinant retrovirus and subsequent flow cytometric selection based on MRK16 antibody staining. Cells were treated in the presence or absence of 25 µM vinblastine and contacted with PE-conjugates mAbs UIC2, MRK16, IgG2a (a negative isotype control) and anti-CD54 (a positive control mAb against a cell surface marker of K562 cells). UIC2 reactivity of this cell line was increased in the presence of the Pgp-transported drug vinblastine, as seen by the rightwards shift in the flow cytometric profile at increasing drug concentrations. This profile shift was not seen with either the positive or negative control mAbs and was not seen with the Pgp-specific mAb MRK16. A similar pattern of mAb binding was observed with FITC-conjugates mAbs and in experiments performed with unlabeled mAbs detected using labeled secondary antibody (sandwich) techniques. In addition, increased UIC2 reactivity was only observed when cells were incubated with drugs and antibody at 37° C., but did not appear when incubations were performed at 4° C. (FIG. 2B), suggesting that enhanced UIC2 binding in the presence of certain Pgp substrates requires the cells to be metabolically active A variety of MDR drugs and competitive inhibitors of Pgp were tested to determine whether these compounds could induce the FACS profile shift observed with UIC2 binding in the presence of vinblastine. The tested compounds included vinblastine, taxol, actinomycin D, gramicidin D, cyclosporine A, reserpine, 5-fluorouracil and methotrexate. The results of these experiments are shown in FIG. 3A for binding of PE-UIC2 mAb and in FIG. 3B for binding of MRK16 mAb. In these experiments, a rightwards shift in the flow cytometry profile of cells contacted with PE-UIC2 mAb was observed for cells treated with vinblastine, taxol, actinomycin D, gramicidin D cyclosporine A and reserpine. No FACS profile shift was observed in cells treated with 5-fluorouracil or methotrexate, supporting the conclusion that shifting was Pgp specific and was specifically induced with Pgp substrates (since neither 5-fluorouracil or methotrexate is (typically) a Pgp substrate). In contrast, and consistent with the earlier results disclosed above, no change in the flow cytometry profile of cells contacted with MRK16 mAb was observed in cells treated with any of the tested drugs. Stimulation of UIC2 reactivity by these compounds was dose-dependent, for some compounds, while for others no shift was observed at any concentration tested (as illustrated in FIG. 4).

Increased UIC2 reactivity in the presence of Pgp substrates was also observed with other Pgp-expressing cells and cell lines, including PA317 cells expressing Pgp via an MDR1-encoding retrovirus(Choi et al., ibid.), NIH 3T3 cells, KB-3-1, VSV 1 and GSV 1 cells transfected with MDR1 cDNA (Choi et al., 1988, *Cell* 53: 519–529), Pgp-positive leukemia/lymphoma and tumor samples and normal B- and T-lymphocyte subpopulations and hematopoietic stem cells expressing Pgp (Chaudhary et al., 1992, Blood ibid.; Chaudhary et al., 1992, *Cell* ibid.). The concentrations of Pgp substrates producing maximal stimulation of UIC2 reactivity differed slightly for different cell lines and appeared to correlate with the levels of Pgp expressed on the corresponding cell lines.

A summary of these results are shown in Table I.

TABLE 1

|  | UIC2 | MRK16 |
|---|---|---|
| MDR Drugs |  |  |
| taxol | + | − |
| vinblastine | + | − |
| reserpine | + | − |
| verapamil | + | − |
| gramicidin | + | − |
| cyclosporine | + | − |
| vincristine | + | − |
| actinomycin D | + | − |
| colchicine* | − | − |
| etoposide* | − | − |
| puromycin | − | − |
| Non-MDR Drugs |  |  |
| 5-fluorouracil | − | − |
| cisplatin | − | − |
| carboplatin | − | − |
| methotrexate | − | − |
| azidothymidine | − | − |
| cyclophosphamide | − | − |

*weak Pgp substrate

EXAMPLE 3

Mutations at Pgp nucleotide-binding Sites Alter UIC2 Reactivity The ability of Pgp transport substrates to increase UIC2 reactivity as described in Example 2 suggested that mAb UIC2 reacts more strongly with Pgp having a conformation associated with functioning (i.e., drug-transporting) Pgp. To investigate the relationship between Pgp function and UIC2 reactivity, nucleotide-binding site mutants of Pgp were used. As described in Example 1, Pgp was mutagenized at highly conserved lysine residues (positions 433 and 1076) in the N-terminal and C-terminal nucleotide-binding sites of the human Pgp. These lysine residues were substituted with methionine residues (i.e., lysine-to-methionine (K-M) substitutions), and the resulting proteins were designated KK (wild-type Pgp), MM (double mutant), KM and MK (C-terminal and N-terminal single mutants, respectively). Analysis of immunoprecipitated Pgps showed that nucleotide binding, as measured by specific photolabeling with $^{32}$P-8-azido-ATP, was decreased in the single mutants (KM and MK) and undetectable in MM (as disclosed in Muller et al., 1996, *J. Biol. Chem.* 271: 1877–1883). In addition, all three mutants (MM, KM and MK) lost detectable ATPase activity (see Muller et al., ibid.). The double mutant, MM, also lost the ability to confer drug resistance to all tested MDR drugs. (including vinblastine and vincristine). KM and MK mutant expressing cells, however, showed a 2–3 fold greater resistance to vinblastine than control cells not expressing Pgp, and accumulated 3–4 times more vinblastine than wildtype (KK)—expressing cells with the same level of vinblastine resistance. Vinblastine resistance conferred by KK, KM and MK Pgps was equally sensitive to inhibition with mAb UIC2.

Figure 5A:
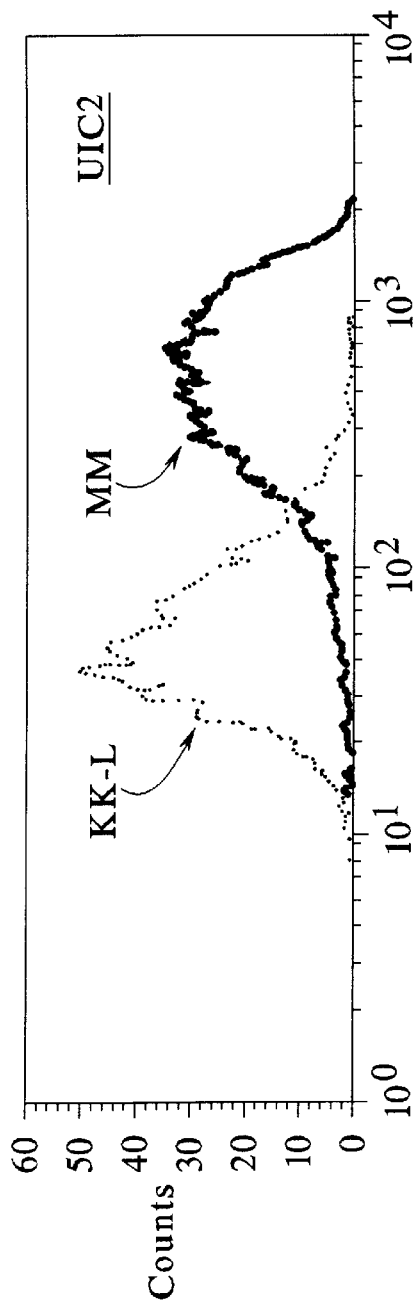
FIGS. 5A through 5D illustrates flow cytometric analysis of mouse L cell transfectants expressing wildtype (KK-L) double mutant (MM) or single mutant (MK-H or KM-H) human Pgp incubated with PE-conjugated UIC2 (FIGS. 5A and 5C) or MRK16 (FIG. 5B or 5D).
Figure 5B:
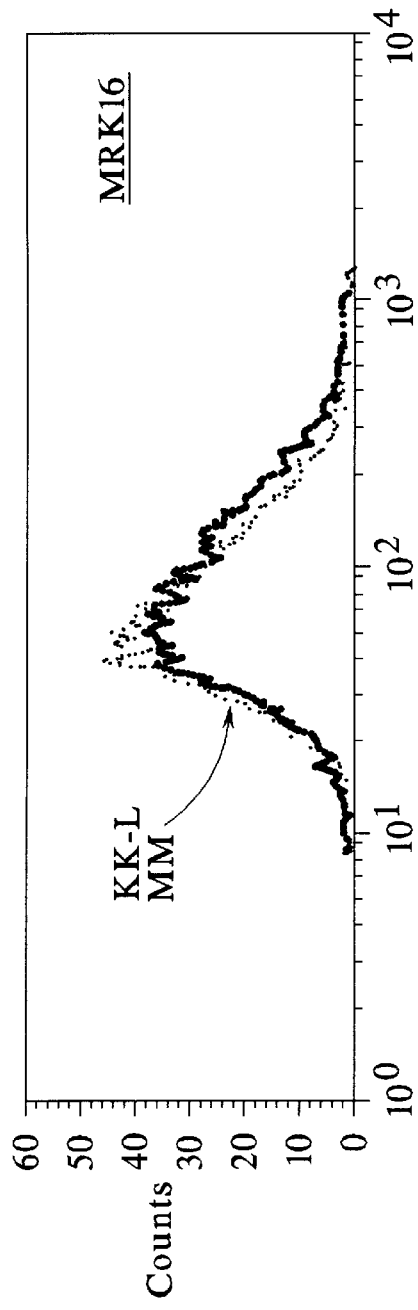
Figure 5C:
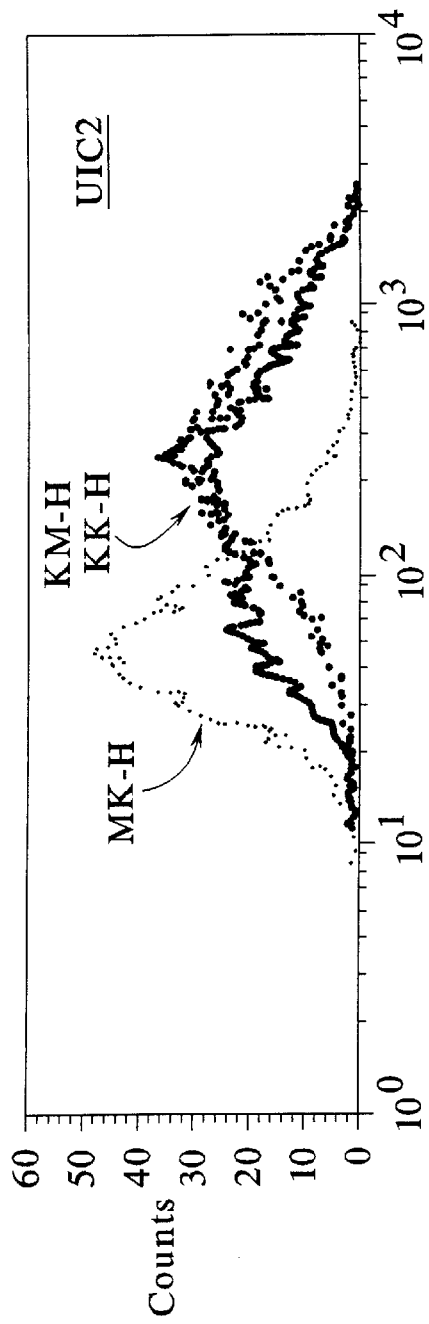
Figure 5D:
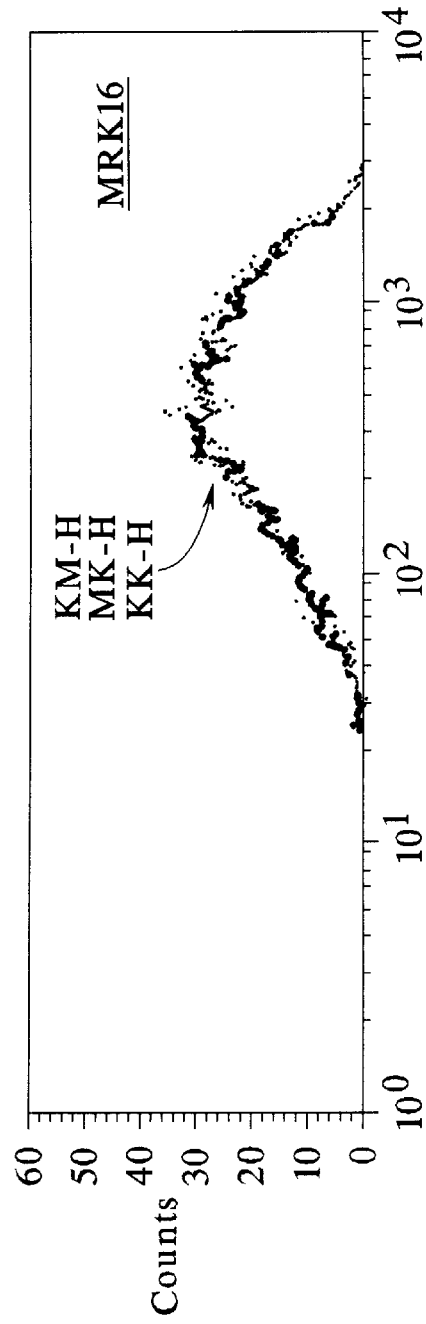

For UIC2 shift experiments, two sets of murine Lmtk-transfectants were used, matched to express very similar levels of the wild-type or mutant human MDR1 Pgps. The first set includes cell lines designated KK-L (wild-type) and MM (double mutant) (FIGS. 5A through 5D and 6A through 6D). The second set, expressing about five times as much Pgp as the first set, includes cell lines KK-H (wild type), KM-H and MK-H (single mutants) (FIGS. 7A through 7F). The relative levels of Pgp expression were established on the basis of indirect immunofluorescence with PE-conjugated FIGS. 5A and 5B show a comparison between flow cytometric analysis of KK-L and MM expressing cells contacted with UIC2 (FIG. 5A) and MRK16 (FIG. 5B). Similarly, FIGS. 5C and 5D show a comparison between flow cytometric analysis of KK-H, MK-H and KM-H expressing cells contacted with UIC2 (FIG. 5C) and MRK16 (FIG. 5D). The flow cytometric pattern of all of these cells was the same when assayed using the MRK16 mAb (see FIGS. 5B and 5D). In contrast to the results obtained using mAb MRK16, UIC2 mAb showed a strikingly different pattern of reactivity with cell lines transfected with mutant Pgps. UIC2 reacted much more strongly with the MM double mutant than with the wild-type Pgp on KK-L cells (compare in FIG. 5A). Similarly, UIC2 binding in single mutant KM-H was equivalent to wildtype binding (KK-H), while the extent of UIC2 binding to the MK-H single mutant was diminished.

Figure 6C:
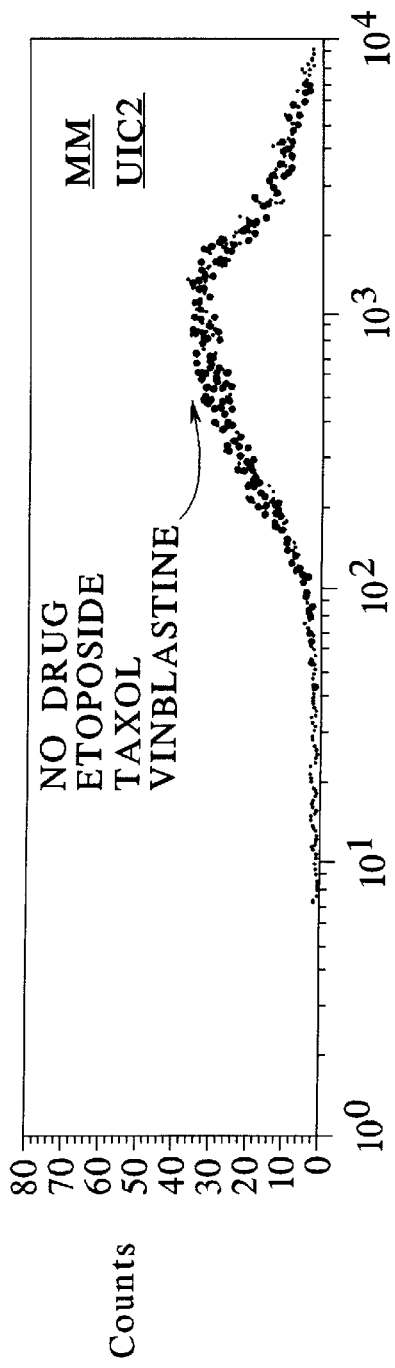
Figure 6D:
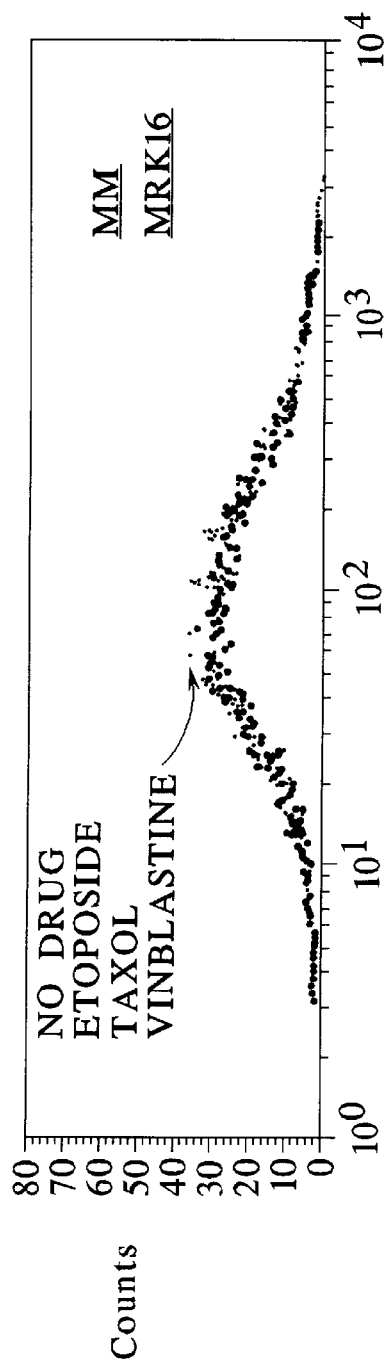
Figure 7C:
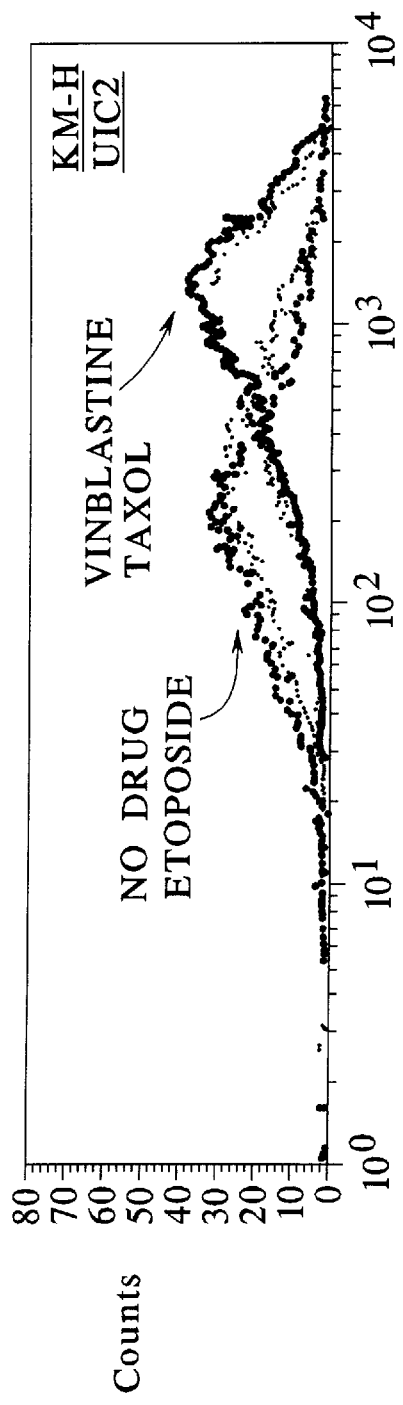
Figure 7D:
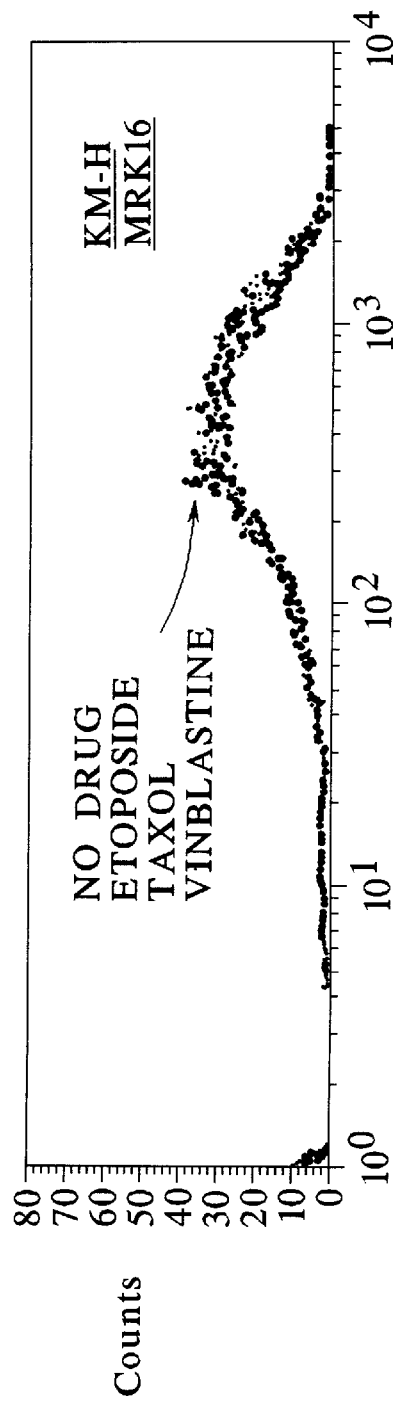

UIC2 mAb binding was compared to MRK16 binding in these cells in the presence or absence of different MDR drugs. These results are shown in FIGS. 6A through 6D. No rightwards shift in the flow cytometric profile was observed in any of the cell lines assayed using MRK16 mAb. In contrast, the wildtype KK-L cell line showed a rightward shift in the profile when cells treated with vinblastine or taxol were assayed, but not when cells treated with etoposide was assayed, consistent with the results disclosed above. The MM double mutant cell line showed no flow cytometric profile shift in the presence of these drugs, but the profile was shifted rightward using UIC2 compared with MRK16 (compare FIGS. 6C and 6D). Vinblastine induced levels of UIC2 mAb reactivity in KK-L cells were roughly equivalent to binding levels seen with MM cells. MM cells showed high levels of UIC2 mAb binding in either the presence or absence of drugs (FIG. 6D); MRK16 binding was unaffected and observed at a level consistent with binding to KK-L cells, confirming our earlier observations on the relative Pgp expression levels of these cell lines.

In contrast with these results, the single mutant MK-H cells showed lower UIC2 reactivity than the wild-type KK-H transfectants, while the reactivity of the other single mutant cell line KM-H, was similar to KK-H (FIGS. 7A through 7F). The KK-H, MK-H and KM-H transfectants were all observed to yield increased UIC2 reactivity by Pgp substrates, with the final levels becoming very similar for all three cell lines (compare FIGS. 7A, 7C and 7E). MRK16 binding levels were approximately the same for all three cell lines in the presence or absence of drug.

These results demonstrated that enhanced UIC2 mAb binding was related to the conformation of Pgp expressed in UIC2-reactive cell lines, and suggested that the MM mutant had adopted a conformation equivalent to the biochemically active conformation presumed to be recognized by UIC2 and which accounted for enhanced UIC2 mAb binding to Pgp in the presence of certain Pgp substrates.

EXAMPLE 4

Intracellular ATP Depletion Maximized UIC2 Reactivity

Figure 8:
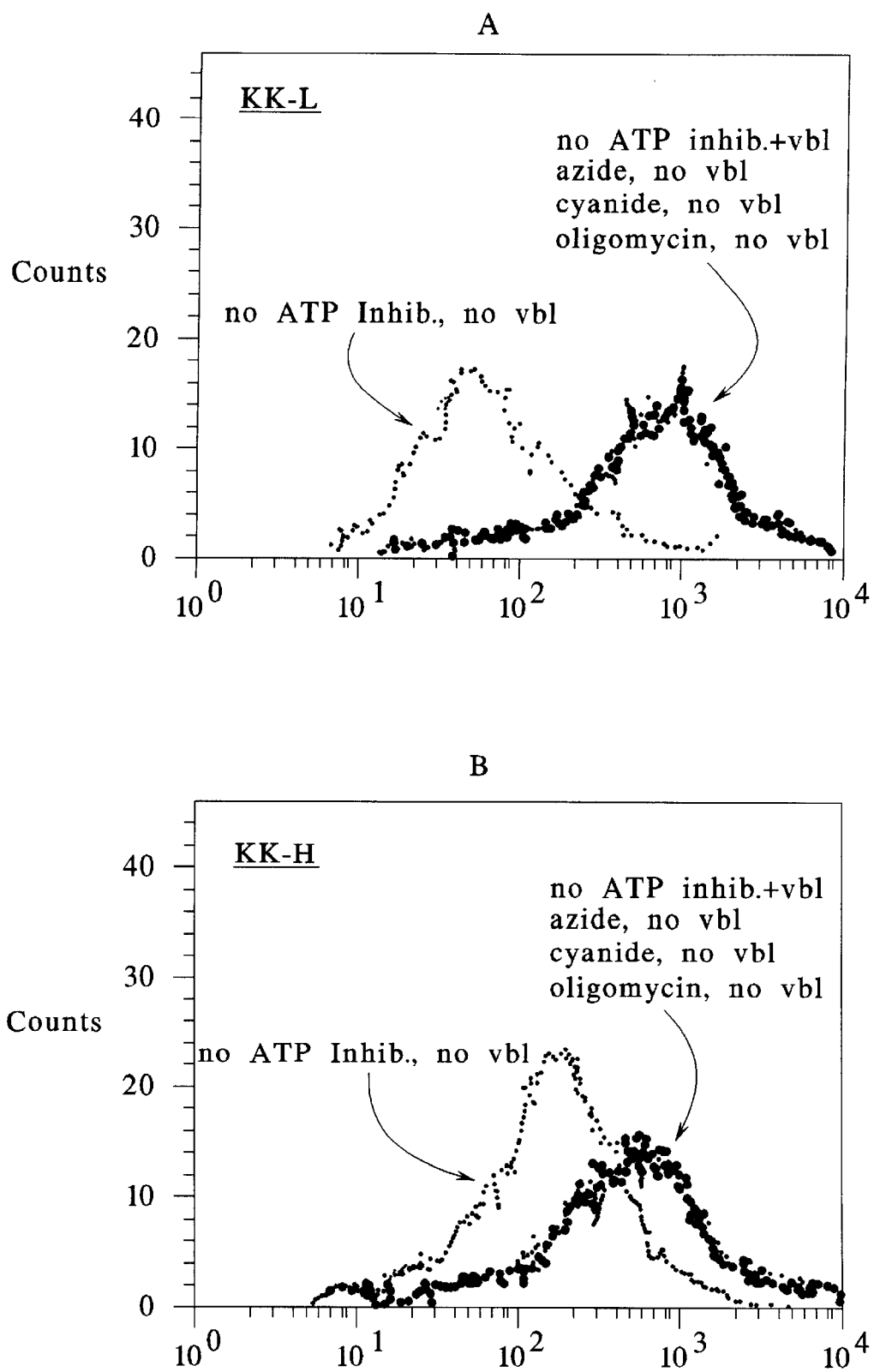
FIGS. 8A through 8E illustrate flow cytometric analysis of mouse L cell transfectants expressing wildtype (KK-L.
Figure 8:
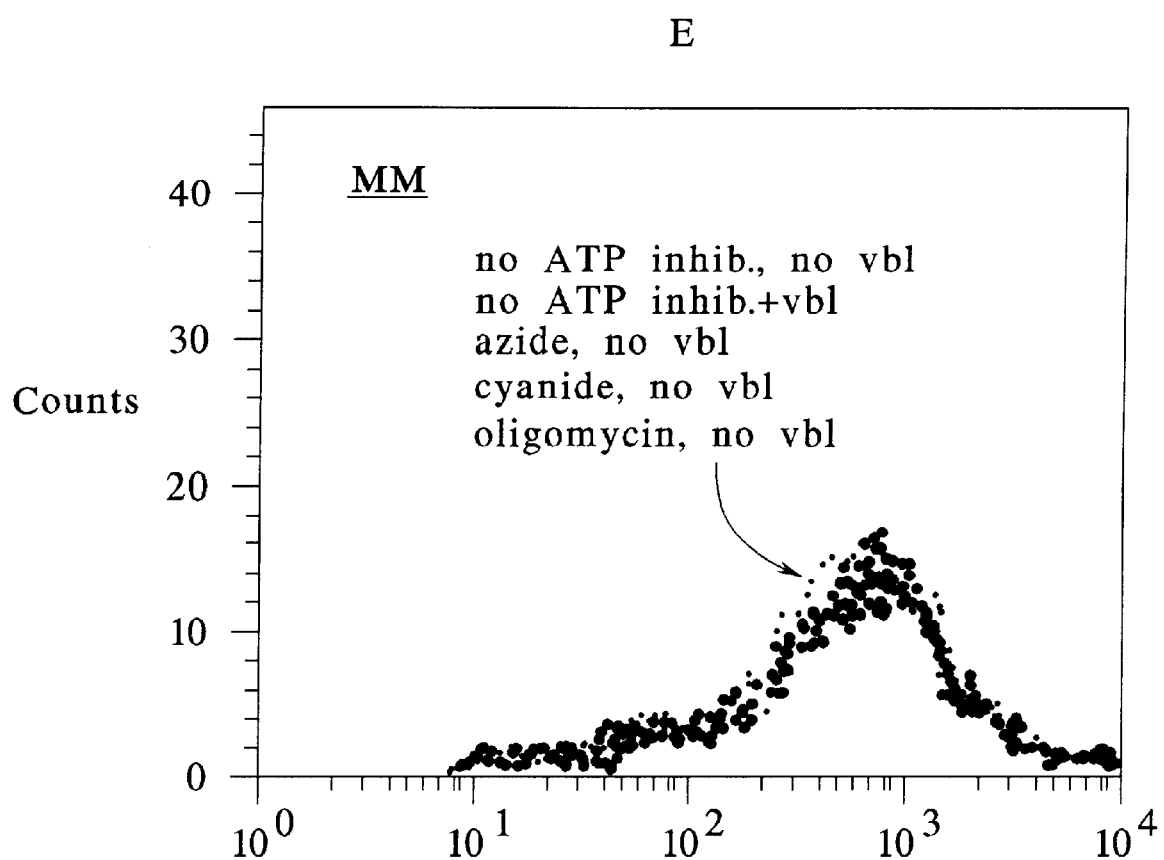
Figure 9A:
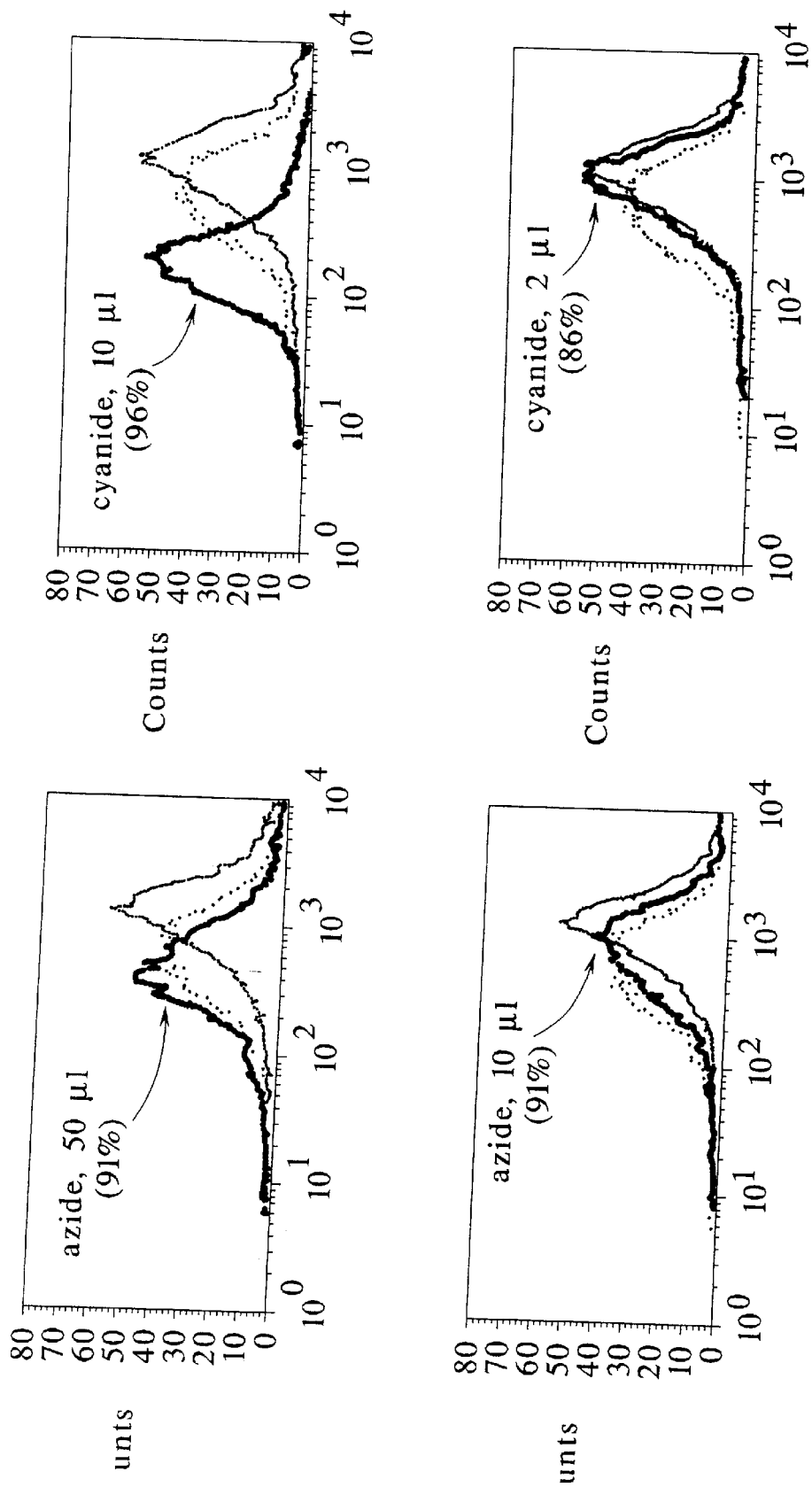
FIGS. 9A through 9C illustrate flow cytometric analysis of K562/i-S9 leukemia cells incubated with PE-conjugated UIC2 in the presence or absence of vinblastine and varying concentrations of the ATP depletion agents oligomycin, azide and cyanide.
Figure 9B:
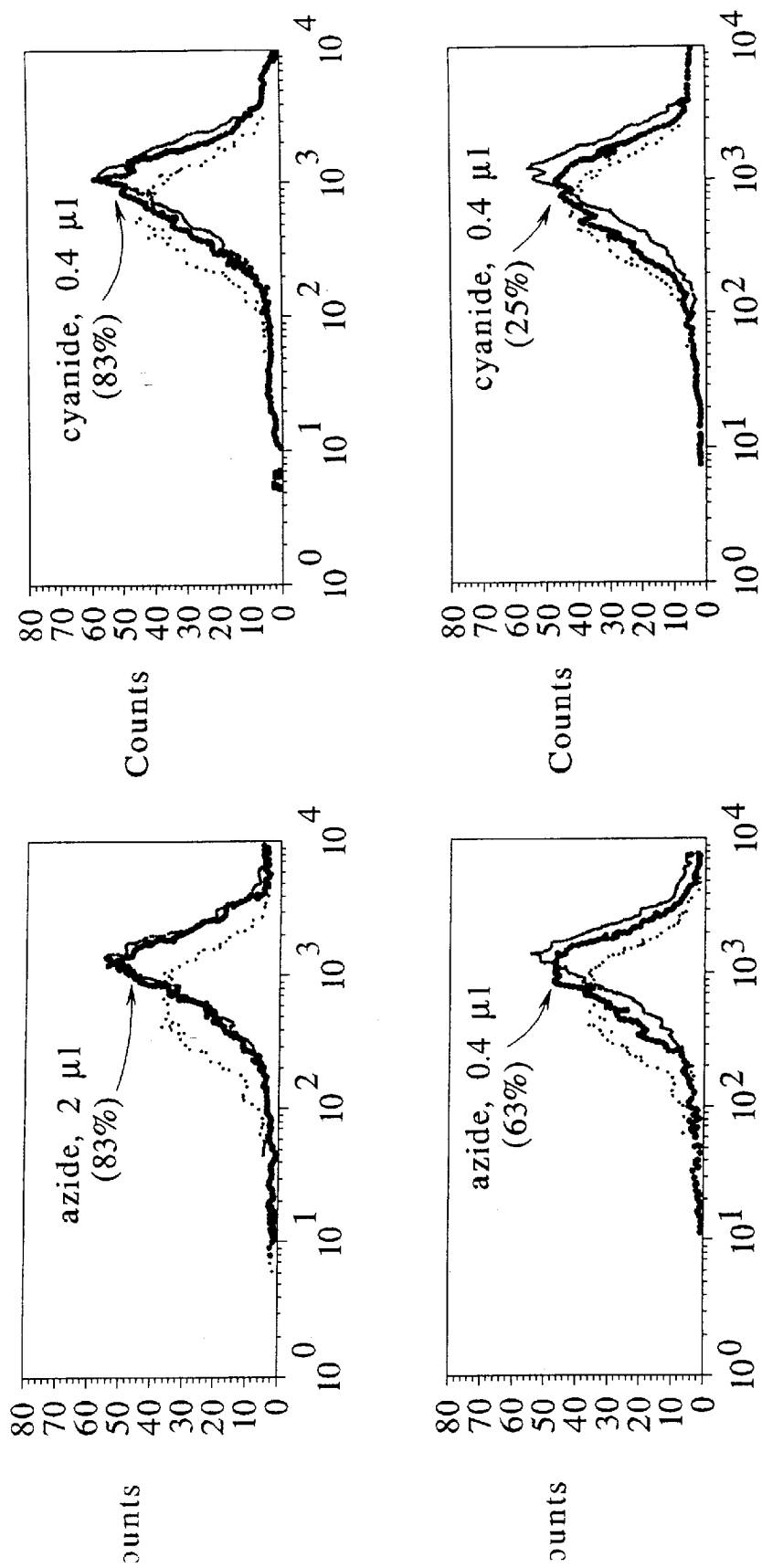
Figure 9C:
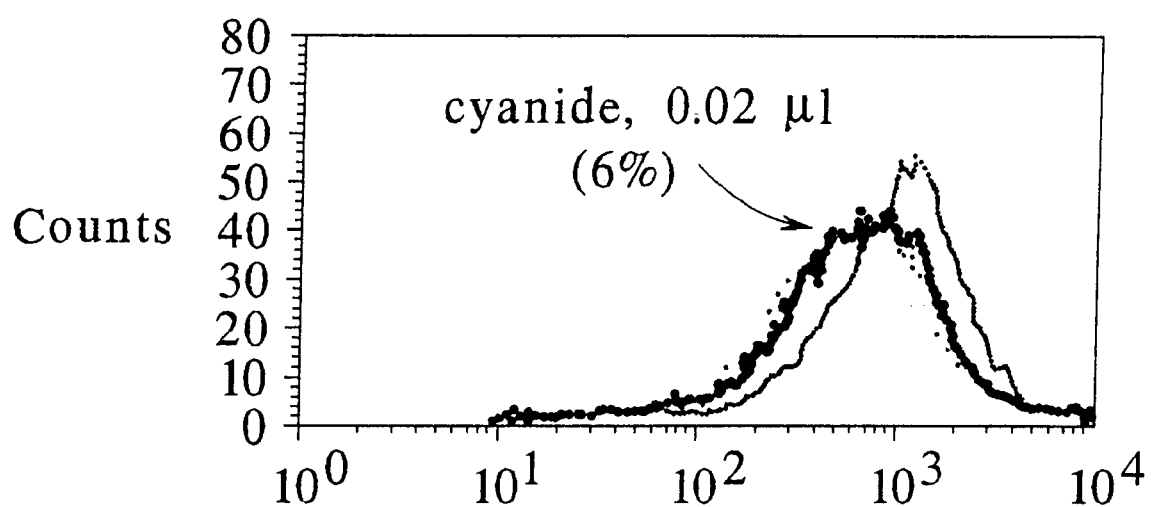

The results described in Example 3 above indicated that maximal UIC2 mAb reactivity was associated with the MM mutant, which carries disabling mutations in both nucleotide-binding sites. This result suggested that the biochemical conformation of Pgp that is specifically recognized by UIC2 mAb could reflect a conformation in which Pgp had no bound ATP. This further suggested that intracellular ATP depleting agents would increase UIC2 mAb reactivity for Pgp. Three different agents that induce ATP depletion, sodium cyanide, sodium azide and oligomycin (all of which are specific for mitochondrial enzymes and mechanisms which generate ATP) were used to deplete Pgp-expressing cells of intracellular ATP. All three agents were found to increase UIC2 mAb reactivity to wild-type Pgp in KK-L (FIG. 8A) and K562/I-S9 cells (FIGS. 9A through 9C). The increase in UIC2 reactivity correlated with the extent of intracellular ATP depletion, as measured by the luciferase assay described in Example 1.

Figure 10A:
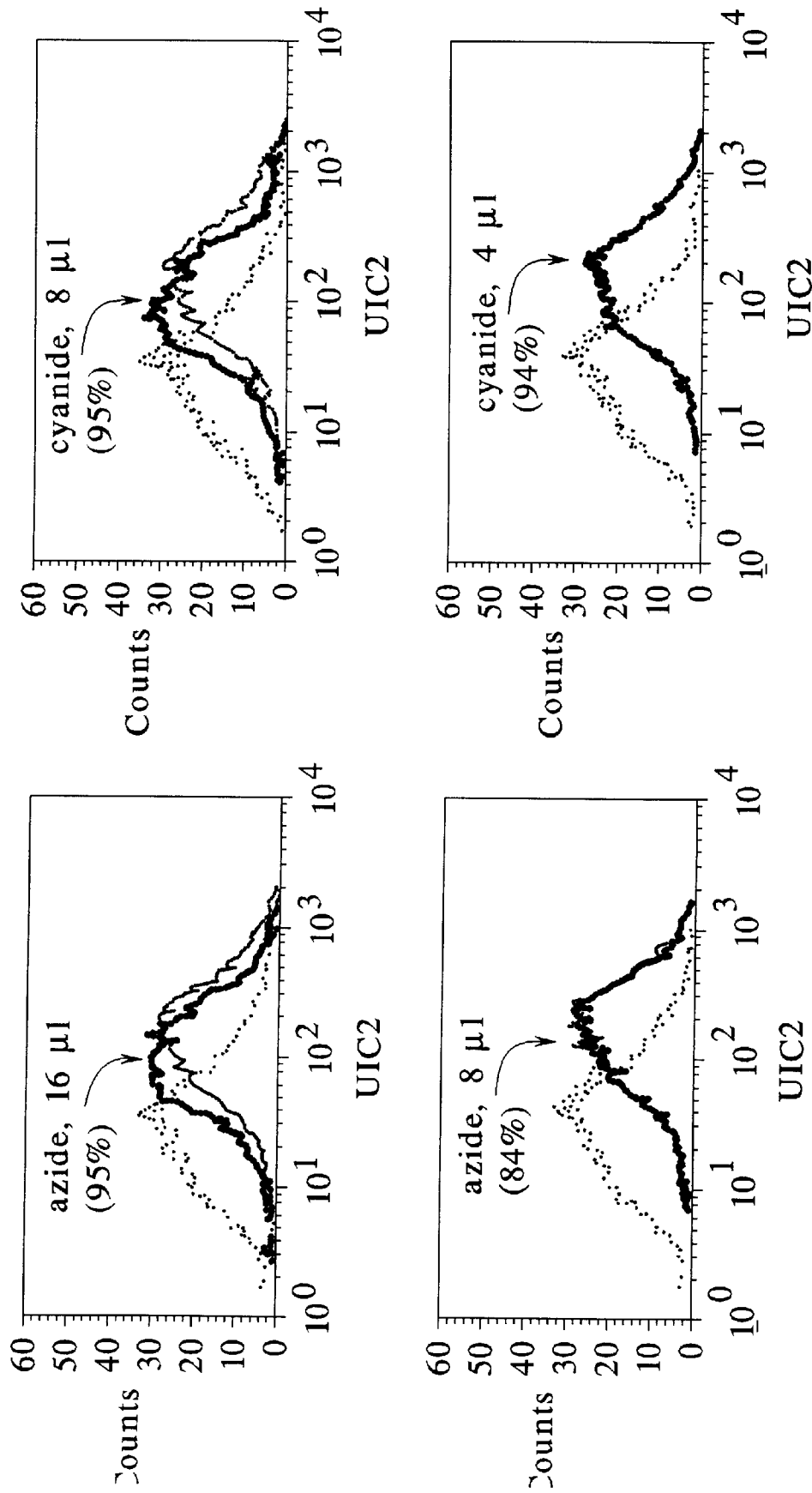
FIGS. 10A and 10B illustrate flow cytometric analysis of KK-L cells incubated with PE-conjugated UIC2 (FIG. 10A) or MRK16 (FIG. 10B) in the presence or absence of vinblastine and varying concentrations of the ATP depletion agents oligomycin, azide and cyanide.
Figure 10A:
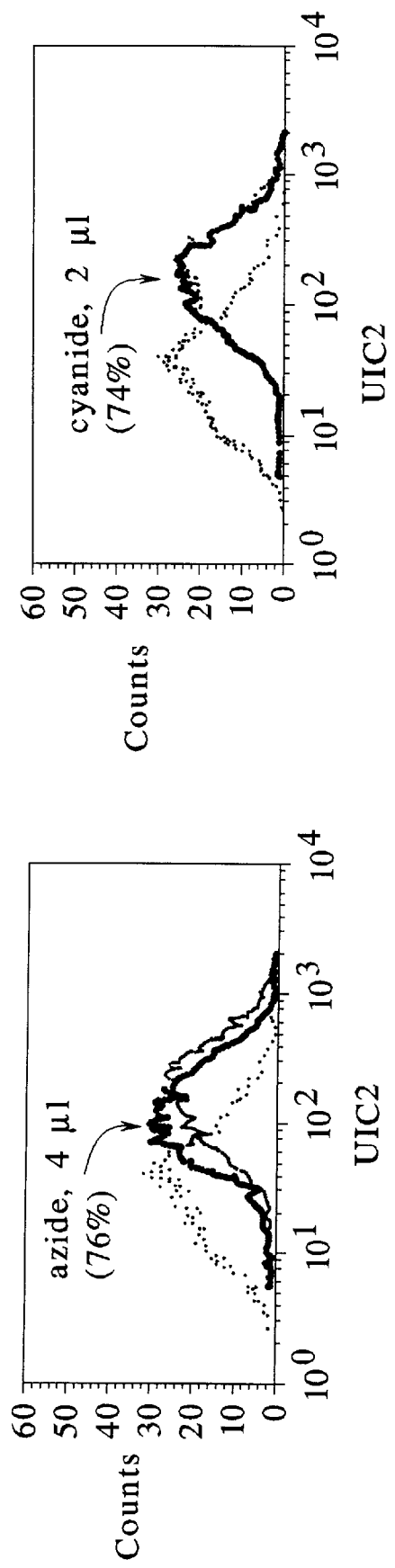
Figure 10B:
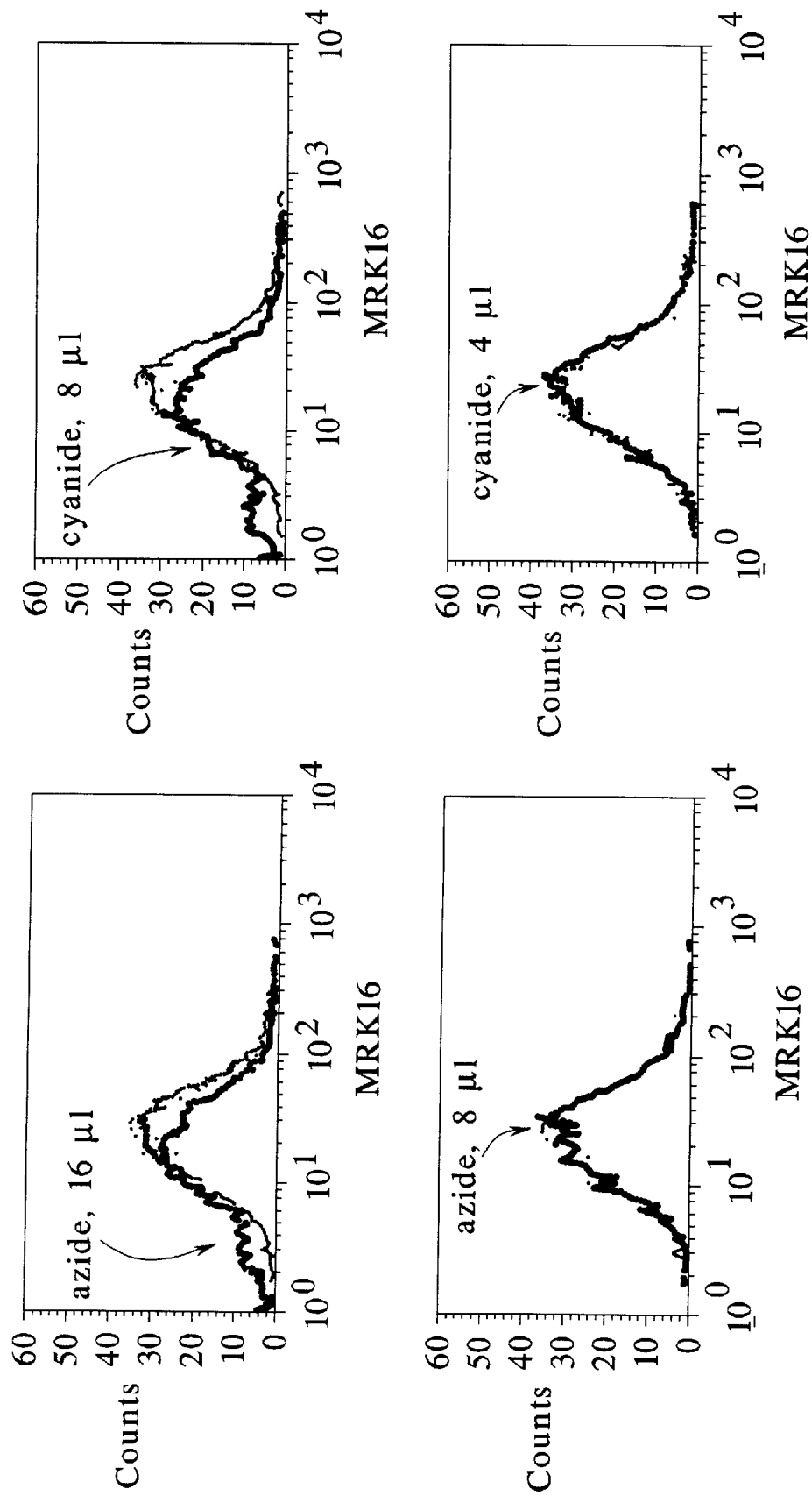
Figure 10B:
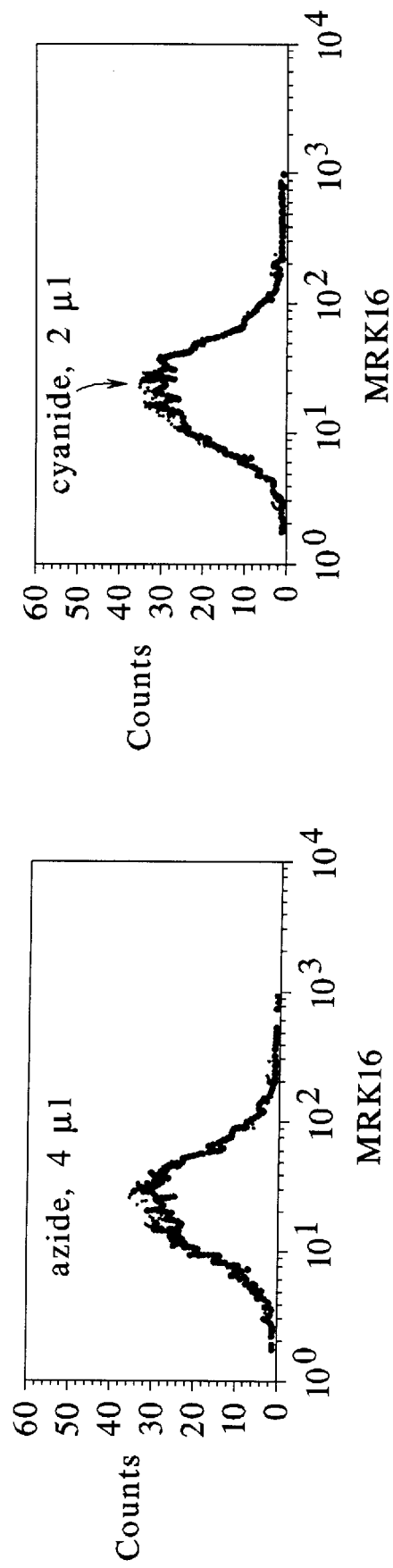

The addition of cyanide, azide or oligomycin to the series of LMtk cells transfected with different Pgp mutants had the same effect on UIC2 mAb reactivity as the addition of Pgp transport substrates (FIGS. 8A through 8E). These agents increased the reactivity of KK-L cells to the level of MM (compare FIGS. 8A and 8B), while having no effect on the MM cell reactivity, and increased the reactivity of KK-H, MK-H and KM-H cell lines to similar final levels. Similar results were obtained in K562/I-S9 cells expressing human Pgp (FIGS. 9A through 9C), and a comparison of UIC2 (FIG. 10A) and MRK16 (FIG. 10B) binding of KK-L cells expressing the wildtype human Pgp is shown in FIGS. 10A and 10B.

Thus, these results support the conclusion that ATP depleting agents have the same effect on UIC2 mAb reactivity as mutagenesis of both nucleotide-binding sites of Pgp.

EXAMPLE 5

Figure 11:
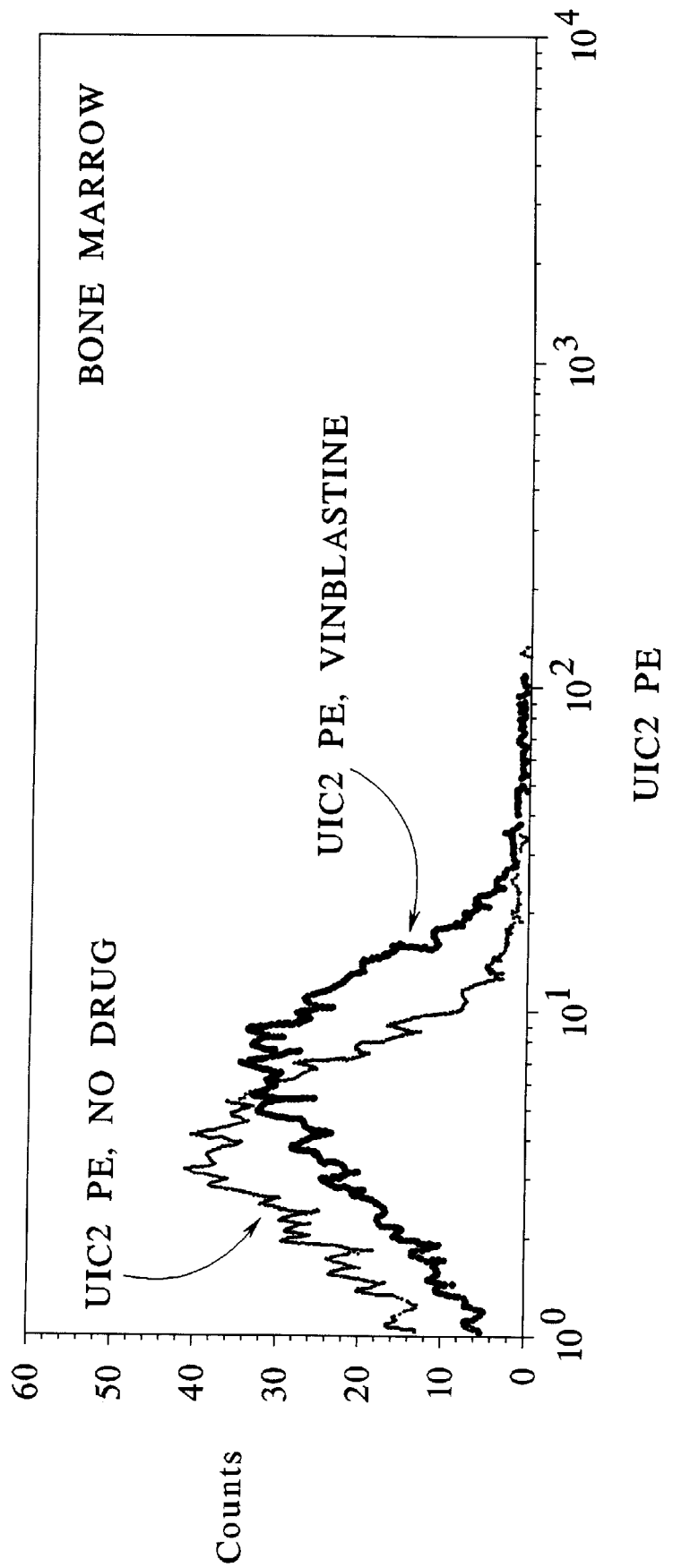
FIG. 11 illustrates a histogram of a 3-color flow cytometric analysis of human bone marrow cells incubated with PE-conjugated UIC2, FITC-conjugated anti-CD38 mAb, and allophycocyanin (APC)-conjugated anti-CD34 mAb, in the presence or absence of vinblastine.
Figure 12:
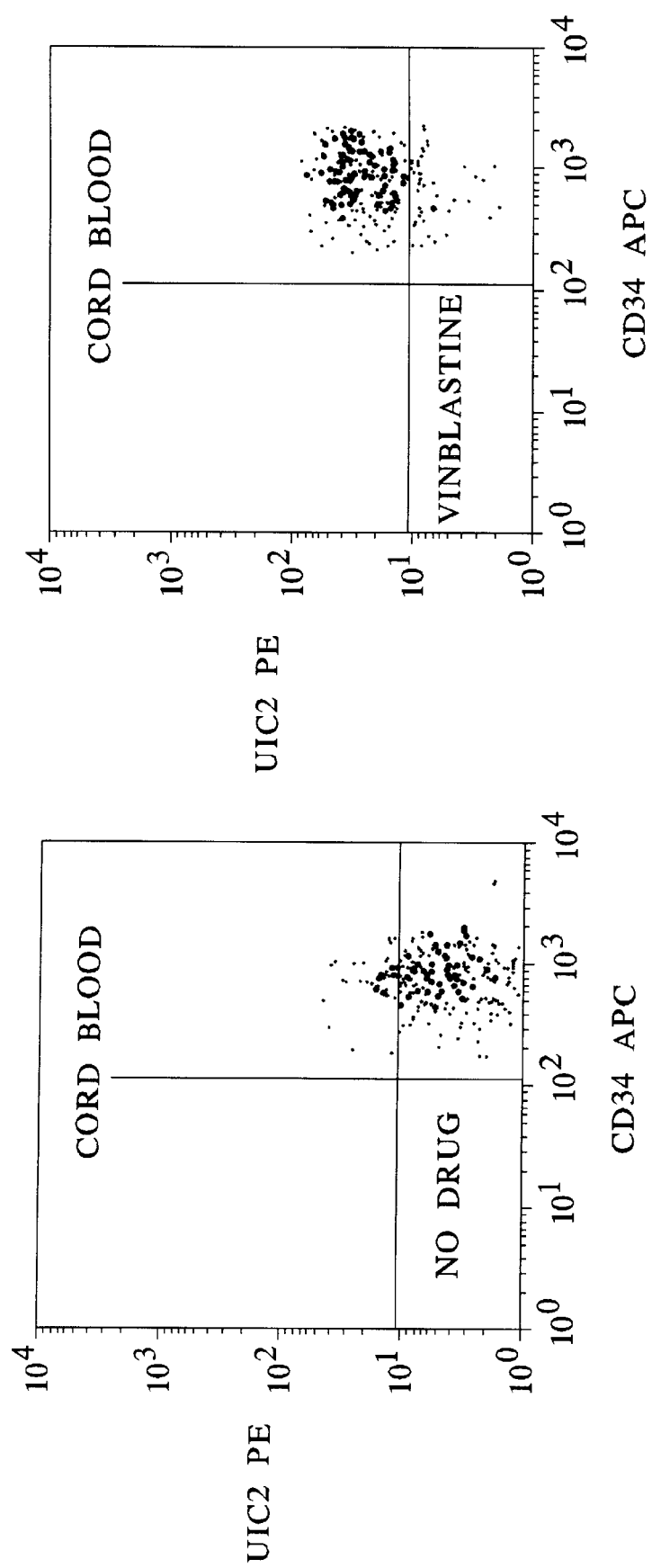
FIG. 12 illustrates a dot plot representing 2-dimensional staining of human umbilical cord blood cells gated to have low expression of CD38, incubated with PE-conjugated UIC2, FITC-conjugated anti-CD38 mAb, and allophycocyanin (APC)-conjugated anti-CD34 mAb, in the presence or absence of vinblastine.

Isolation and detection of hematopoietic stem cells using UIC2 Hematopoietic stem cells were isolated from bone marrow and umbilical cord blood using the methods of the invention. FIGS. 11 (bone marrow) and 12(cord blood) show the results of 3-color flow cytometry (by FACS Vantage, BDIS) analysis of human bone marrow and umbilical cord blood samples. The cells were stained with (1) PE-conjugated UIC2, (2) FITC-conjugated anti-CD38 mAb, and (3) allophycocyanin (APC)-conjugated anti-CD34 mAb, in the presence or absence of vinblastine. The enhanced (up to 10-fold) binding of UIC2 mAb to bone marrow and cord blood stem cells was observed in the presence of vinblastine, proving that the described phenomenon can be used for improved labeling of stem cells with UIC2 and their consequent purification by conventional separation techniques.

It should be understood that the foregoing disclosure emphasizes certain specific embodiments of the invention and that all modifications or alternatives equivalent thereto are within the spirit and scope of the invention as set forth in the appended claims.

What is claimed is:

1. A method for producing an antibody or antigen binding fragment thereof specific for P-glycoprotein in a biochemical conformation adopted in the presence of Pgp-mediated transport substrates or ATP depleting agents, the method comprising the steps of introducing a cell expressing a heterologous, mutant P-glycoprotein into an animal syngeneic with the species from which the cell was derived, wherein the heterologous, mutant P-glycoprotein is in a biochemical conformation adopted in the presence of Pgp-mediated transport substrates or ATP depleting agents, and wherein the heterologous, mutant P-glycoprotein has an amino acid sequence encoded by human MDR1 except that the sequence comprises an amino acid residue at positions 433 and 1076 of the Pgp amino acid sequence that is independently changed to methionine, and producing immune cells in the animal expressing an antibody specific for P-glycoprotein in said biochemical conformation.

2. The method of claim 1 further comprising producing a hybridoma cell line that expresses a monoclonal antibody specific for P-glycoprotein in a biochemical conformation adopted in the presence of Pgp-mediated transport substrates or ATP depleting agents.

3. The method of claim 1 wherein the heterologous P-glycoprotein comprises an amino acid sequence identified as SEQ ID NO: 2.

* * * * *